United States Patent [19]

Meyhack et al.

[11] Patent Number: 5,175,105

[45] Date of Patent: Dec. 29, 1992

[54] **PROCESS FOR THE PRODUCTION OF UROKINASE USING *SACCHAROMYES CEREVISIAE***

[75] Inventors: Bernd Meyhack, Magden; Jutta Heim, Pratten; Rolf Bürgi, Basel, all of Switzerland

[73] Assignee: Ciba-Geigy Corporation, Ardsley, N.Y.

[21] Appl. No.: 179,345

[22] Filed: Apr. 8, 1988

[30] Foreign Application Priority Data

| Apr. 15, 1987 | [GB] | United Kingdom | 8709081 |
| Jun. 16, 1987 | [GB] | United Kingdom | 8714059 |
| Dec. 4, 1987 | [IE] | Ireland | 3299/87 |

[51] Int. Cl.⁵ .................. C12N 15/58; C12N 1/19; C12N 15/81; C12N 9/72
[52] U.S. Cl. .................. 435/215; 435/256; 435/320.1
[58] Field of Search .................. 435/212, 215, 71.1, 435/69.1, 320.1; 935/27; 536/27

[56] References Cited

U.S. PATENT DOCUMENTS

| 4,245,051 | 1/1981 | Reich et al. | 435/212 |
| 4,370,417 | 1/1983 | Hung et al. | 435/212 |
| 4,558,010 | 12/1985 | Hung et al. | 435/212 |
| 5,010,003 | 4/1991 | Chang | 435/69.9 |

FOREIGN PATENT DOCUMENTS

| 0037687 | 10/1981 | European Pat. Off. |
| 41766 | 12/1981 | European Pat. Off. |
| 88632 | 9/1983 | European Pat. Off. |
| 93619 | 11/1983 | European Pat. Off. |
| 1005612 | 2/1984 | European Pat. Off. |
| 123544 | 10/1984 | European Pat. Off. |
| 154272 | 9/1985 | European Pat. Off. |
| 174835 | 3/1986 | European Pat. Off. |

OTHER PUBLICATIONS

Lijnen et al. Biochemica Biophysica Acta 884 pp. 402–408 (1986).
Research Disclosure—Oct. 1987, No. 282.
Abstract RD-282-004-A Sep. 20, 1987.
Edited by Philip J. Barr et al., Yeast Genetic Engineering, Chapter 14, Anthony J. Brake, pp. 269–280 (1989).
Flohe, European Heart J., 6, pp. 905–908 (1985).
Winkler et al. Biochemistry, 25, 4041–4045 (1986).
Riccio et al. Nucl. Acids Research, 13, pp. 2759–2771 (1985).
Magai et al., Gene, 36, pp. 183–188 (1985).
Jacobs et al., D.N.A. 4, pp. 139–146 (1985).
Ratzkin et al., Proc. Natl. Acad. Sci. U.S.A., 78, pp. 3313–3317 (1981).
Chemical Abstracts, 100, p. 1512 (1984).
B. Meyhack et al., 786 Esperientia, vol. 38, p. 745 (1982).
Mujanohara et al., Proc. Natl. Acad. Sci. U.S.A. vol. 80, pp. 1–5, Jan. 1983.
Arima et al., Nucleic Acids Research, vol. 11, No. 6 (1983).
Pennica et al., Nature, vol. 301, pp. 214–221 Jan. 20, 1983.
Edlund et al, Proc. Natl. Acad. Sci U.S.A. vol. 80, pp. 349–352 (Jan. 1983).
Wallen et al., Eur. J. Biochem., vol. 132, pp. 681–686 (1983).
Ryken et al., J. Biological Chemistry, vol. 250, No. 13, pp. 7035–7041 (1981).
Meyhack et al., The Embo Journal, vol. 1, No. 6, pp. 675–680 (1982).

*Primary Examiner*—Richard A. Schwartz
*Assistant Examiner*—Nancy T. Vogel
*Attorney, Agent, or Firm*—JoAnn Villamizar

[57] ABSTRACT

Novel human plasminogen activators of the urokinase type are produced by yeast cells transformed with a hybrid vector comprising a DNA sequence coding for said human plasminogen activator. Novel hybrid vectors, yeast hosts transformed with such hybrid vectors and processes for the production thereof are also provided.

4 Claims, 16 Drawing Sheets

FIG. 2A

```
  1 CCCGGGCTCCGGGCTGCGGTCTCCTGCCGCAGCCACCGAGCCGCCGTCTAGCGCCCCGA

MET ARG ALA LEU LEU ALA ARG LEU LEU LEU CYS VAL     -9
 60 CCTCGCCACC ATG AGA GCC CTG CTG GCG CGC CTG CTT CTC TGC GTC

LEU VAL VAL SER ASP SER LYS GLY SER ASN GLU LEU HIS GLN VAL   7
106  CTG GTC GTG AGC GAC TCC AAA GGC AGC AAT GAA CTT CAT CAA GTT

PRO SER ASN CYS ASP CYS LEU ASN GLY GLY THR CYS VAL SER ASN  22
151  CCA TCG AAC TGT GAC TGT CTA AAT GGA GGA ACA TGT GTG TCC AAC

LYS TYR PHE SER ASN ILE HIS TRP CYS ASN CYS PRO LYS LYS PHE  37
196  AAG TAC TTC TCC AAC ATT CAC TGG TGC AAC TGC CCA AAG AAA TTC

GLY GLY GLN HIS CYS GLU ILE ASP LYS SER LYS THR CYS TYR GLU  52
241  GGA GGG CAG CAC TGT GAA ATA GAT AAG TCA AAA ACC TGC TAT GAG

GLY ASN GLY HIS PHE TYR ARG GLY LYS ALA SER THR ASP THR MET  67
286  GGG AAT GGT CAC TTT TAC CGA GGA AAG GCC AGC ACT GAC ACC ATG

GLY ARG PRO CYS LEU PRO TRP ASN SER ALA THR VAL LEU GLN GLN  82
331  GGC CGG CCC TGC CTG CCC TGG AAC TCT GCC ACT GTC CTT CAG CAA

THR TYR HIS ALA HIS ARG SER ASP ALA LEU GLN LEU GLY LEU GLY  97
376  ACG TAC CAT GCC CAC AGA TCT GAT GCT CTT CAG CTG GGC CTG GGG

LYS HIS ASN TYR CYS ARG ASN PRO ASP ASN ARG ARG ARG PRO TRP 112
421  AAA CAT AAT TAC TGC AGG AAC CCA GAC AAC CGG AGG CGA CCC TGG

CYS TYR VAL GLN VAL GLY LEU LYS PRO LEU VAL GLN GLU CYS MET 127
466  TGC TAT GTG CAG GTG GGC CTA AAG CCG CTT GTC CAA GAG TGC ATG

VAL HIS ASP CYS ALA ASP GLY LYS LYS PRO SER SER PRO PRO GLU 142
511  GTG CAT GAC TGC GCA GAT GGA AAA AAG CCC TCC TCT CCT CCA GAA

GLU LEU LYS PHE GLN CYS GLY GLN LYS THR LEU ARG PRO ARG PHE 157
556  GAA TTA AAA TTT CAG TGT GGC CAA AAG ACT CTG AGG CCC CGC TTT

LYS ILE ILE GLY GLY GLU PHE THR THR ILE GLU ASN GLN PRO TRP 172
601  AAG ATT ATT GGG GGA GAA TTC ACC ACC ATC GAG AAC CAG CCC TGG

PHE ALA ALA ILE TYR ARG ARG HIS ARG GLY GLY SER VAL THR TYR 187
646  TTT GCG GCC ATC TAC AGG AGG CAC CGG GGG GGC TCT GTC ACC TAC

VAL CYS GLY GLY SER LEU ILE SER PRO CYS TRP VAL ILE SER ALA 202
691  GTG TGT GGA GGC AGC CTC ATC AGC CCT TGC TGG GTG ATC AGC GCC
```

FIG. 2B

```
        THR HIS CYS PHE ILE ASP TYR PRO LYS LYS GLU ASP TYR ILE VAL    217
    736 ACA CAC TGC TTC ATT GAT TAC CCA AAG AAG GAG GAC TAC ATC GTC

TYR LEU GLY ARG SER ARG LEU ASN SER ASN THR GLN GLY GLU MET    232
    781 TAC CTG GGT CGC TCA AGG CTT AAC TCC AAC ACG CAA GGG GAG ATG

LYS PHE GLU VAL GLU ASN LEU ILE LEU HIS LYS ASP TYR SER ALA    247
    826 AAG TTT GAG GTG GAA AAC CTC ATC CTA CAC AAG GAC TAC AGC GCT

ASP THR LEU ALA HIS HIS ASN ASP ILE ALA LEU LEU LYS ILE ARG    262
    871 GAC ACG CTT GCT CAC CAC AAC GAC ATT GCC TTG CTG AAG ATC CGT

SER LYS GLU GLY ARG CYS ALA GLN PRO SER ARG THR ILE GLN THR    277
    916 TCC AAG GAG GGC AGG TGT GCG CAG CCA TCC CGG ACT ATA CAG ACC

ILE CYS LEU PRO SER MET TYR ASN ASP PRO GLN PHE GLY THR SER    292
    961 ATC TGC CTG CCC TCG ATG TAT AAC GAT CCC CAG TTT GGC ACA AGC

CYS GLU ILE THR GLY PHE GLY LYS GLU ASN SER THR ASP TYR LEU    307
   1006 TGT GAG ATC ACT GGC TTT GGA AAA GAG AAT TCT ACC GAC TAT CTC

TYR PRO GLU GLN LEU LYS MET THR VAL VAL LYS LEU ILE SER HIS    322
   1051 TAT CCG GAG CAG CTG AAA ATG ACT GTT GTG AAG CTG ATT TCC CAC

ARG GLU CYS GLN GLN PRO HIS TYR TYR GLY SER GLU VAL THR THR    337
   1096 CGG GAG TGT CAG CAG CCC CAC TAC TAC GGC TCT GAA GTC ACC ACC

LYS MET LEU CYS ALA ALA ASP PRO GLN TRP LYS THR ASP SER CYS    352
   1141 AAA ATG CTG TGT GCT GCT GAC CCA CAG TGG AAA ACA GAT TCC TGC

GLN GLY ASP SER GLY GLY PRO LEU VAL CYS SER LEU GLN GLY ARG    367
   1186 CAG GGA GAC TCA GGG GGA CCC CTC GTC TGT TCC CTC CAA GGC CGC

MET THR LEU THR GLY ILE VAL SER TRP GLY ARG GLY CYS ALA LEU    382
   1231 ATG ACT TTG ACT GGA ATT GTG AGC TGG GGC CGT GGA TGT GCC CTG

LYS ASP LYS PRO GLY VAL TYR THR ARG VAL SER HIS PHE LEU PRO    397
   1276 AAG GAC AAG CCA GGC GTC TAC ACG AGA GTC TCA CAC TTC TTA CCC

TRP ILE ARG SER HIS THR LYS GLU GLU ASN GLY LEU ALA LEU        411
   1321 TGG ATC CGC AGT CAC ACC AAG GAA GAG AAT GGC CTG GCC CTC TGA

1366 GGGTCCCCAGGGAGGAAACGGGCACCACCCGCTTTCTTGCTGGTTGTCATTTTTGCAGTA

1426 GAGTCATCTCCATCAGCTGTAAGAAGAGACTGGGAAGATAGGCTCTGCACAGATGGATTT

1486 GCCTGTGGCACCACCAGGGTGAACGACAATAGCTTTACCCTCACGGATAGGCCTGGGTGC

1546 TGGCTGCCCAGACCCTCTGGCCAGGATGGAGGGGTGGTCCTGACTCAACATGTTACTGAC

1606 CAGCAACTTGTCTTTTTCTGGACTGAAGCCTGCAGGAGTTAAAAAGGGCAGGGCATCTCC
```

FIG. 2C

```
1666 TGTGCATGGGCTCGAAGGGAGAGCCAGCTCCCCCGACCGGTGGGCATTTGTGAGGCCCAT

1726 GGTTGAGAAATGAATAATTTCCCAATTAGGAAGTGTAAGCAGCTGAGGTCTCTTGAGGGA

1786 GCTTAGCCAATGTGGGAGCAGCGGTTTGGGGAGCAGAGACACTAACGACTTCAGGGCAGG

1846 GCTCTGATATTCCATGAATGTATCAGGAAATATATATGTGTGTATGTTTGCACACTTG

1906 TTGTGTGGGCTGTGAGTGTAAGTGTGAGTAAGAGCTGGTGTCTGATTGTTAAGTCTAAAT

1966 ATTTCCTTAAACTGTGTGGACTGTGATGCCACACAGAGTGGTCTTTCTGGAGAGGTTATA

2026 GGTCACTCCTGGGGCCTCTTGGGTCCCCCACGTGACAGTGCCTGGGAATGTACTTATTCT

2086 GCAGCATGACCTGTGACCAGCACTGTCTCAGTTTCACTTTCACATAGATGTCCCTTTCTT

2146 GGCCAGTTATCCCTTCCTTTTAGCCTAGTTCATCCAATCCTCACTGGGTGGGGTGAGGAC

2206 CACTCCTTACACTGAATATTTATATTTCACTATTTTATTTATATTTTTGTAATTTTAAA

2266 TAAAAGTGATCAATAAAATGTGATTTTTCTG(A)n
```

FIG. 3
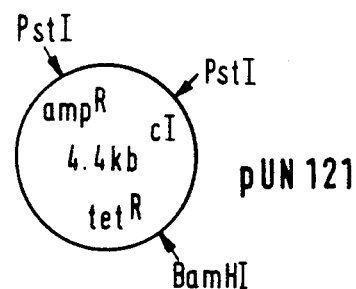
1. BamHI, PstI digests
2. isolation of 1.5kb fragment
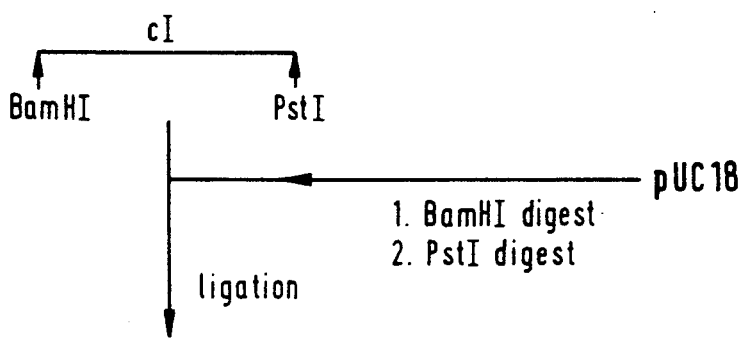
1. PstI digest
2. T4 DNA polymerase
3. XhoI linker ligation
4. XhoI digest
5. recircularization
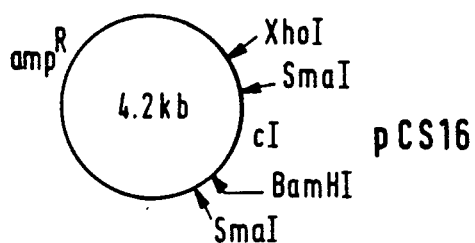

FIG. 6

```
     TaqI    -670        -660        -650        -640
        TCGAGT TTATCATTAT CAATACTCGC CATTTCAAAG AATACGTAAA
-630        -620        -610        -600        -590
     TAATTAATAG TAGTGATTTT CCTAACTTTA TTTAGTCAAA AAATTAGCCT
-580        -570        -560        -550        -540
     TTTAATTCTG CTGTAACCCG TACATGCCAA AATAGGGGGC GGGTTACACA
-530        -520        -510        -500        -490
     GAATATATAA CATCGTAGGT GTCTGGGTGA ACAGTTTATT CCTGGCATCC
-480        -470        -460        -450        -440
     ACTAAATATA ATGGAGCCCG CTTTTAAGC TGGCATCCAG AAAAAAAAAG
-430        -420        -410        -400        -390
     AATCCCAGCA CCAAAATATT GTTTTCTTCA CCAACCATCA GTTCATAGGT
-380        -370        -360        -350        -340
     CCATTCTCTT AGCGCAACTA CAGAGAACAG GGGCACAAAC AGGCAAAAAA
-330        -320        -310        -300        -290
     CGGGCACAAC CTCAATGGAG TGATGCAACC TGCCTGGAGT AAATGATGAC
-280        -270        -260        -250        -240
     ACAAGGCAAT TGACCCACGC ATGTATCTAT CTCATTTTCT TACACCTTCT
-230        -220        -210        -200        -190
     ATTACCTTCT GCTCTCTCTG ATTTGGAAAA AGCTGAAAAA AAAGGTTGAA
-180        -170        -160        -150        -140
     ACCAGTTCCC TGAAATTATT CCCCTACTTG ACTAATAAGT ATATAAAGAC
-130        -120        -110        -100         -90
     GGTAGGTATT GATTGTAATT CTGTAAATCT ATTTCTTAAA CTTCTTAAAT
 -80         -70         -60        -50 DraI    -40
     TCTACTTTTA TAGTTAGTCT TTTTTTTAGT TTTAAAACAC CAAGAACTTA
 -30 TaqI    -20         -10         -1
     GTTTCGAATA AACACACATA AATAAACAAA ATG
```

FIG. 8 a. p31GAPFL-IT                                    −198

5'-GATCT CCCTGAAAAA AAAGGTTGAA
ACCAGTTCCC TGAAATTATT CCCCTACTTG ACTAATAAGT ATATAAAGAC
GGTAGGTATT GATTGTAATT CTGTAAATCT ATTTCTTAAA CTTCTTAAAT
TCTACTTTTA TAGTTAGTCT TTTTTTTAGT TTTAAAACAC CAAGAACTTA
GTTTCGAATA AACACACATA AATAAAG-3'
                                                   −5 b. p31GAPEL-IT
            −263

5'-GATCTCCCGC ATGTATCTAT CTCATTTTCT TACACCTTCT
ATTACCTTCT GCTCTCTCTG ATTTGGAAAA AGCTGAAAAA AAAGGTTGAA
ACCAGTTCCC TGAAATTATT CCCCTACTTG ACTAATAAGT ATATAAAGAC
GGTAGGTATT GATTGTAATT CTGTAAATCT ATTTCTTAAA CTTCTTAAAT
TCTACTTTTA TAGTTAGTCT TTTTTTTAGT TTTAAAACAC CAAGAACTTA
GTTTCGAATA AACACACATA AATAAAG-3'
                                                   −5 c. p31GAPDL-IT
      −540

5'-GATCTCC GGGTTACACA GAATATATAA CATCGTAGGT GTCTGGGTGA
ACAGTTTATT CCTGGCATCC ACTAAATATA ATGGAGCCCG CTTTTTAAGC
TGGCATCCAG AAAAAAAAAG AATCCCAGCA CCAAAATATT GTTTTCTTCA
CCAACCATCA GTTCATAGGT CCATTCTCTT AGCGCAACTA CAGAGAACAG
GGCACAAAC AGGCAAAAAA CGGGCACAAC CTCAATGGAG TGATGCAACC
TGCCTGGAGT AAATGATGAC ACAAGGCAAT TGACCCACGC ATGTATCTAT
CTCATTTTCT TACACCTTCT ATTACCTTCT GCTCTCTCTG ATTTGGAAAA
AGCTGAAAAA AAAGGTTGAA ACCAGTTCCC TGAAATTATT CCCCTACTTG
ACTAATAAGT ATATAAAGAC GGTAGGTATT GATTGTAATT CTGTAAATCT
ATTTCTTAAA CTTCTTAAAT TCTACTTTTA TAGTTAGTCT TTTTTTTAGT
TTTAAAACAC CAAGAACTTA GTTTCGAATA AACACACATA AATAAAG-3'
                                                   −5

FIG. 13A

|  | $X_1$ | $X_2$ |  | $Y_1$ | $Y_2$ | $Y_3$ |  | $Z_1$ |  | $Z_2$ |

Mature scu-PA

| 1 |  | 135 |  |  | 157 |  |  | 302 |  | 411 |
|---|---|---|---|---|---|---|---|---|---|---|
| Ser | —— | Gly | Lys | Lys | —— | Arg | Phe | Lys | Ile | —— | Asn | Ser | Thr | —— | Leu |
| AGC | —— | GGA | AAA | AAG | —— | CGC | TTT | AAG | ATT | —— | AAT | TCT | ACC | —— | CTC |

1. [Gly135]-scu-PA

| 1 |  | 135 |  |  | 157 |  |  | 302 |  | 411 |
|---|---|---|---|---|---|---|---|---|---|---|
| Ser | —— | Gly | Gly | Lys | —— | Arg | Phe | Lys | Ile | —— | Asn | Ser | Thr | —— | Leu |
| AGC | —— | GGA | GGT | AAG | —— | CGC | TTT | AAG | ATT | —— | AAT | TCT | ACC | —— | CTC |

2. [Ser135]-scu-PA

| 1 |  | 135 |  |  | 157 |  |  | 302 |  | 411 |
|---|---|---|---|---|---|---|---|---|---|---|
| Ser | —— | Gly | Ser | Lys | —— | Arg | Phe | Lys | Ile | —— | Asn | Ser | Thr | —— | Leu |
| AGC | —— | GGA | AGT | AAG | —— | CGC | TTT | AAG | ATT | —— | AAT | TCT | ACC | —— | CTC |

3. [Asp157]-scu-PA

| 1 |  | 135 |  |  | 157 |  |  | 302 |  | 411 |
|---|---|---|---|---|---|---|---|---|---|---|
| Ser | —— | Gly | Lys | Lys | —— | Arg | Asp | Lys | Ile | —— | Asn | Ser | Thr | —— | Leu |
| AGC | —— | GGA | AAA | AAG | —— | CGC | GAC | AAG | ATT | —— | AAT | TCT | ACC | —— | CTC |

4. [Gln302]-scu-PA

| 1 |  | 135 |  |  | 157 |  |  | 302 |  | 411 |
|---|---|---|---|---|---|---|---|---|---|---|
| Ser | —— | Gly | Lys | Lys | —— | Arg | Phe | Lys | Ile | —— | Gln | Ser | Thr | —— | Leu |
| AGC | —— | GGA | AAA | AAG | —— | CGC | TTT | AAG | ATT | —— | CAA | TCT | ACC | —— | CTC |

5. [Gly135,Asp157]-scu-PA

| 1 |  | 135 |  |  | 157 |  |  | 302 |  | 411 |
|---|---|---|---|---|---|---|---|---|---|---|
| Ser | —— | Gly | Gly | Lys | —— | Arg | Asp | Lys | Ile | —— | Asn | Ser | Thr | —— | Leu |
| AGC | —— | GGA | GGT | AAG | —— | CGC | GAC | AAG | ATT | —— | AAT | TCT | ACC | —— | CTC |

FIG. 13B

6. [Ser135,Asp157]-scu-PA

| 1 | | 135 | | | 157 | | | | 302 | | | 411 |
|---|---|---|---|---|---|---|---|---|---|---|---|---|
| Ser | —— | Gly Ser Lys | —— | Arg Asp Lys Ile | —— | Asn Ser Thr | —— | Leu |
| AGC | —— | GGA AGT AAG | —— | CGC GAC AAG ATT | —— | AAT TCT ACC | —— | CTC |

7. [Gly135,Asp157,Gln302]-scu-PA

| 1 | | 135 | | 157 | | 302 | | 411 |
|---|---|---|---|---|---|---|---|---|
| Ser | —— | Gly Gly Lys | —— | Arg Asp Lys Ile | —— | Gln Ser Thr | —— | Leu |
| AGC | —— | GGA GGT AAG | —— | CGC GAC AAG ATT | —— | CAA TCT ACC | —— | CTC |

8. [Ser135,Asp157,Gln302]-scu-PA

| 1 | | 135 | | 157 | | 302 | | 411 |
|---|---|---|---|---|---|---|---|---|
| Ser | —— | Gly Ser Lys | —— | Arg Asp Lys Ile | —— | Gln Ser Thr | —— | Leu |
| AGC | —— | GGA AGT AAG | —— | CGC GAC AAG ATT | —— | CAA TCT ACC | —— | CTC |

PROCESS FOR THE PRODUCTION OF UROKINASE USING *SACCHAROMYES CEREVISIAE*

The invention concerns a novel process for the production of proteins, more especially serine proteases of the urokinase type. Said process includes the use of genetically engineered yeast strains. The invention concerns furthermore novel urokinase-type proteins, DNAs encoding such proteins, hybrid vectors containing such DNAs, said genetically engineered yeast strains and processes for the production of said DNAs, hybrid vectors and yeast strains.

Urokinase or urokinase-type plasminogen activator (hereinafter referred to as "u-PA") is a serine protease which activates plasminogen to plasmin by proteolytic cleavage. Plasmin is a potent protease which is able to degrade the fibrin network of blood clots to form soluble degradation products.

u-PA was first isolated from human urine and is also known to be secreted by cultured kidney cells and some tumour cell lines. It is initially produced as a single chain molecule (hereinafter referred to as "scu-PA") and can be proteolytically converted by the action of plasmin to a two chain form (hereinafter referred to as "tcu-PA") in which the two chains remain attached to each other via a disulfide bridge. u-PA has a unique glycosylation site at Asn302.

Since scu-PA has only inferior amidolytic activity against low molecular weight synthetic substrates it was regarded until recently as a true proteolytically inactive precursor of the active enzyme tcu-PA. Most recent results, however, prove that scu-PA efficiently activates plasminogen to plasmin and has a considerably higher selectivity for fibrin than tcu-PA [cf. H. R. Lijnen et al., J.Biol.Chem. 261, 1253 (1986)]. The mechanisms of the surprising fibrinolytic activity and the clot specificity of scu-PA have been studied [Lijnen et al. supra; D. Collen et al. J.Biol.Chem. 261, 1259 (1986)]. It was demonstrated that scu-PA is not an inactive zymogen but activates plasminogen without being previously transformed into tcu-PA. Unlike tcu-PA, scu-PA is competitively inhibited by a yet unknown plasma component which inhibition is reversed by fibrin or fibrin fragments, i.e. at the clot. While circulating in blood under in vivo conditions scu-PA does therefore not activate plasminogen. Its fibrinolytic activity remains restricted to its proper target. On the contrary, tcu-PA is capable of activating plasminogen at any point within the circulatory system, thereby leading to undesirable side effects such as hemorrhage. These properties render scu-PA the preferred urokinase-type plasminogen activator.

With the advent of recombinant DNA technology it is now possible to produce proteins such as scu-PA on industrial scale. Based on the known structure of genomic u-PA DNA [A. Riccio et al. Nucleic Acids Research 13, 2759 (1985)] and u-PA cDNA [W. E. Holmes et al. Biotechnology 3, 923 (1985)] processes for the production of scu-PA which make use of recombinant DNA technology have been described in the literature. Thus, expression in *E. coli* has been achieved by W. E. Holmes et al. (supra), P. Jacobs et al. [DNA 4, 139 (1985)], M. E. Winkler et al. [Biochemistry 25, 4041 (1986)], M. Nagai et al. [Gene 36, 183 (1985)]; see also Belgian Patent No. 900 826, Japanese Patent No. 61 181 377, and European Patent Application No. 92 182. The expression of scu-PA in animal cells is disclosed in European Patent Applications No. 92 182 and 154 272. However, all of these known processes suffer from weighty disadvantages: It has been proven difficult to grow animal cells on a large scale which is a prerequisite for the cheap and profitable manufacture of proteins produced by these cells. The generation time of animals cells is considerably higher than that of microorganisms, thus requiring a prolonged fermentation period in order to obtain a sufficiently high cell density. The cell density, in turn, obtainable in the cultivation of animal cells is considerably lower than the cell density generally reached in large scale cultivation of microorganisms. Moreover, strain improvements are difficult to achieve as compared to microorganisms. On the other hand, contaminating endotoxins are often found in protein preparations from *E. coli*. These have to be eliminated by expensive and time-consuming purification steps. Proteins produced by *E. coli* are necessarily unglycosylated because *E. coli* is devoid of the enzymatic system which is responsible for the attachment of carbohydrate chains to appropriate sites in the protein molecule. Recombinant scu-PA is therefore, unlike natural scu-PA, unglycosylated when produced by *E. coli*. It was reported that scu-PA produced by *E. coli* exists as an amorphous insoluble polymer, due to an imperfect alignment of the disulfide bridges and to an incorrect folding of the protein. At least one additional refolding step involving large quantities of solvent is thus required in order to obtain a biologically active protein (M. E. Winkler et al., supra).

Considering the drawbacks of the known processes there is a continued need for improved methods which render possible the production of biologically active and scu-PA on a large scale. It is an object of the present invention to provide such methods.

It has surprisingly been found that yeast cells transformed with a hybrid vector carrying the human u-PA coding sequence attached to the signal sequence of a yeast gene produce scu-PA which has a biological activity equivalent to that of natural scu-PA and is yeast specifically glycosylated. It is noteworthy that yeast scu-PA is completely active without any in vitro refolding procedures being required.

Accordingly, the invention concerns a method for the production of human single chain urokinase-type plasminogen activator or a mutant thereof comprising culturing under appropriate nutrient conditions a yeast strain transformed with a hybrid vector comprising a yeast expression control sequence, a DNA segment consisting of a first DNA sequence encoding a signal peptide upstream of and in reading frame with a second DNA sequence coding for mature urokinase-type plasminogen activator or a mutant thereof, which DNA segment is under transcriptional control of said expression control sequence, and a DNA sequence comprising transcription termination signals of a yeast gene, and isolating said urokinase-type plasminogen activator or mutant thereof.

The term "DNA sequence coding for mature urokinase-type plasminogen activator" is intended to embrace all allelic forms of u-PA which are known to exist in or can be isolated from the human genome. These DNA sequences are devoid of any pre- and/or pro-sequences.

Mutants of scu-PA are especially those mutants which render the protein protease resistant. Such scu-PA mutants are covalently modified at sites of proteolysis by proteases occurring in blood such as thrombin or plasmin, so that they are no longer susceptible to protease hydrolysis at these locations. The target sites include Lys135 to Lys136 (cleavage at this site generates the so-called low molecular weight form of scu-PA or LUK; see FIG. 2 of the accompanying drawings), Arg156 to Phe157 (susceptible to thrombin attack) and Lys158 to Ile159 (cleavage at this site by plasmin generates tcu-PA). Suitable scu-PA mutants have site specific substitutions, insertions or deletions of amino acid residues at one or more of these target sites. Especially preferred are those mutants in which one amino acid residue or both amino acid residues forming the target sites are deleted or in which at least one of these amino acid residues is replaced by another amino acid residue so that the resulting mutants are resistant to proteolytic attack.

In further mutants of scu-PA the unique N-glycosylation site occurring at $Asn^{302}$ ($Asn^{302}$-Ser-Thr) is modified such that glycosylation cannot take place at this site. It is well established that a prerequisited for N-linked glycosylation in mammalian cells is the occurrence of the tripeptide sequence -Asn-L-Thr(or Ser)- wherein Asn is the acceptor and L can be any of the 20 genetically encoded amino acids except proline or aspartic acid which impede glycosylation.

The term "scu-PA proteins" whenever used hereinbefore or hereinafter is intended to include scu-PA as well as mutants thereof.

The invention relates especially to a method for the production of scu-PA proteins having the formula I acids, such as acidic amino acid residues, for example the residues of glutamic acid and aspartic acid, basic amino acid residues, for example the residues of arginine, lysine and histidine, and neutral amino acid residues, for example the residues of asparagine, glutamine, glycine, alanine, leucine, isoleucine, serine, threonine, tyrosine or proline.

In order to prevent glycosylation at the N-glycosylation site the tripeptide sequences recognised as signal for N-glycosylation has to be altered. Replacement of the Asn ($Z_1$) and/or Thr ($Z_2$) residues in the above tripeptide sequence by any other amino acid would abolish formation of glycosidic linkages at this site. For convenience, modification of the N-glycosylation site is not done at the protein level. Instead, it is advantageous to modify the gene coding for scu-PA in such a way that upon expression of said modified gene by a host a mutant scu-PA is produced in which the N-glycosylation site is altered in such a way that glycosylation cannot take place at this site. Especially, asparagine is substituted with valine, leucine, isoleucine, alanine or, in particular, glutamine, and threonine with valine, methionine or, in particular, alanine.

In a preferred embodiment the present invention relates to a process for the production of compounds of the formula I in which $X_1$ is Lys, Gly or Ser, $X_2$ represents Lys, $Y_1$ is Arg, $Y_2$ is Phe, Asp or Glu, $Y_3$ is Lys, $Z_1$ is Asn or Gln and $Z_2$ is Thr.

Especially, the invention relates to a process for the production of scu-PA, [Gly135]-scu-PA, [Ser135]-scu-PA, [Asp157]-scu-PA, [Ser135,Asp157]-scu-PA and

```
Pro  Ser  Asn  Cys  Asp  Cys  Leu  Asn       Ser  Asn  Glu  Leu  His  Gln  Val
Cys  Val  Ser  Asn
Lys  Tyr  Phe  Ser  Asn  Ile  His  Trp  Cys  Asn  Cys  Pro  Lys  Lys  Phe  Asn
Gly  Gly  Gln  His  Cys  Glu  Ile  Asp  Lys  Ser  Lys  Thr  Cys  Tyr  Glu  Gln
Gly  Asn  Gly  His  Phe  Tyr  Arg  Gly  Lys  Ala  Ser  Thr  Asp  Thr  Met  Gln
Gly  Arg  Pro  Cys  Leu  Pro  Trp  Asn  Ser  Ala  Thr  Val  Leu  Gln  Gln  Thr
Tyr  His  Ala  His  Arg  Ser  Asp  Ala  Leu  Gln  Leu  Gly  Leu  Gly  Lys
His  Asn  Tyr  Cys  Arg  Asn  Pro  Asp  Asn  Arg  Arg  Arg  Pro  Trp
Cys  Tyr  Val  Gln  Val  Gly  Leu  Lys  Pro  Leu  Val  Gln  Glu  Cys  Met  Val
His  Asp  Cys  Ala  Asp  Gly  $X_1$  $X_2$  Pro  Ser  Ser  Pro  Pro  Glu  Glu
Leu  Lys  Phe  Gln  Cys  Gly  Gln  Lys  Thr  Leu  Arg  Pro  $Y_1$  $Y_2$  $Y_3$
Ile  Ile  Gly  Gly  Glu  Phe  Thr  Thr  Ile  Glu  Asn  Gln  Pro  Trp
Phe  Ala  Ala  Ile  Tyr  Arg  Arg  His  Arg  Gly  Gly  Ser  Val  Thr  Tyr
Val  Cys  Gly  Gly  Ser  Leu  Ile  Ser  Pro  Cys  Trp  Val  Ile  Ser  Ala
Thr  His  Cys  Phe  Ile  Asp  Tyr  Pro  Lys  Lys  Glu  Asp  Tyr  Ile  Val
Tyr  Leu  Gly  Arg  Ser  Arg  Leu  Asn  Ser  Asn  Thr  Gln  Gly  Glu  Met
Lys  Phe  Glu  Val  Glu  Asn  Leu  Ile  Leu  His  Lys  Asp  Tyr  Ser  Ala
Asp  Thr  Leu  Ala  His  His  Asn  Asp  Ile  Ala  Leu  Leu  Lys  Ile  Arg
Ser  Lys  Glu  Gly  Arg  Cys  Ala  Gln  Pro  Ser  Arg  Thr  Ile  Gln  Thr
Ile  Cys  Leu  Pro  Ser  Met  Tyr  Asn  Asp  Pro  Gln  Phe  Gly  Thr  Ser
Cys  Glu  Ile  Thr  Gly  Phe  Gly  Lys  Glu  $Z_1$  Ser  $Z_2$  Asp  Tyr  Leu
Tyr  Pro  Glu  Gln  Leu  Lys  Met  Thr  Val  Val  Lys  Leu  Ile  Ser  His
Arg  Glu  Cys  Gln  Gln  Pro  His  Tyr  Tyr  Gly  Ser  Glu  Val  Thr  Thr
Lys  Met  Leu  Cys  Ala  Ala  Asp  Pro  Gln  Trp  Lys  Thr  Asp  Ser  Cys
Gln  Gly  Asp  Ser  Gly  Gly  Pro  Leu  Val  Cys  Ser  Leu  Gln  Gly  Arg
Met  Thr  Leu  Thr  Gly  Ile  Val  Ser  Trp  Gly  Arg  Gly  Cys  Ala  Leu
Lys  Asp  Lys  Pro  Gly  Val  Tyr  Thr  Arg  Val  Ser  His  Phe  Leu  Pro
Trp  Ile  Arg  Ser  His  Thr  Lys  Glu  Glu  Asn  Gly  Leu  Ala  Leu
``` in which $X_1$ and $X_2$ independently from each other represent Lys, an amino acid residue other than a basic amino acid residue or a chemical bond, $Y_1$ is Arg, an amino acid residue other than a basic amino acid residue or a chemical bond, $Y_2$ is Phe, an acidic amino acid residue or a chemical bond, $Y_3$ is Lys, an amino acid residue other than a basic amino acid residue or a chemical bond, $Z_1$ is Asn which is yeast-specifically glycosylated, or is another amino acid residue, and $Z_2$ is Thr or another amino acid residue different from Ser.

The term "amino acid residue" is intended to embrace the residues of all genetically encoded amino

[Gly135,Asp157]-scu-PA wherein $Asn^{302}$ is yeast specifically glycosylated, and furthermore [Gln302]-scu-PA, [Gly135,Asp157,Gln302]-scu-PA and [Ser135,Asp157,Gln302]-scu-PA.

The transformed yeast strains according to the invention are cultured in a liquid medium containing assimilable sources of carbon, nitrogen and inorganic salts.

Various carbon sources are usable. Examples of preferred carbon sources are assimilable carbohydrates, such as glucose, maltose, mannitol or lactose, or an acetate such as sodium acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate, which can be used either alone or in suitable mixtures. Inorganic salts which may be used include, for example, sulphates, chlorides, phosphates and carbonates of sodium, potassium, magnesium and calcium. Additionally, the nutrient medium may also contain growth promoting substances. Substances which promote growth include, for example, trace elements, such as iron, zinc, manganese and the like, or individual amino acids.

Yeast cells containing hybrid plasmids with a constitutive promoter (e.g. ADHI, GAPDH) express the u-PA gene attached to said promoter without induction. However, if the u-PA gene is under the control of a regulated promoter (e.g. PGK or PH05) the composition of the growth medium has to be adapted in order to obtain maximum levels of mRNA transcripts, i.e. when using the PH05 promoter the growth medium must contain a low concentration of inorganic phosphate for derepression of this promoter.

The cultivation is carried out by employing conventional techniques. The culturing conditions, such as temperature, pH of the medium and fermentation time are selected in such a way that maximal levels of scu-PA proteins are produced. A chosen yeast strain is preferably grown under aerobic conditions in submerged culture with shaking or stirring at a temperature of about 25° to 35° C., preferably at about 28° C., at a pH value of from 4 to 7, for example at approximately pH 5, and for about 20 to 50 hours, preferably until maximum yields of scu-PA proteins are reached.

The produced scu-PA protein can accumulate within the yeast cells or can be secreted into the periplasmic space. In case the scu-PA protein has accumulated within the cells, the first step for the recovery of the scu-PA protein consists in liberating the protein from the cell interior. In most procedures the cell wall is first removed by enzymatic digestion with glucosidases (infra). Subsequently, the resulting spheroplasts are treated with detergents, such as Triton ® X-100. Alternatively, mechanical forces, such as shearing forces (for example X-press, French-press) or shaking with glass beads, are suitable for breaking cells. The resulting mixture is enriched for scu-PA protein by conventional means, such as removal of most of the non-proteinaceous material by treatment with polyethyleneimine, precipitation of the proteins using ammonium sulphate, gel electrophoresis, dialysis, chromatography, for example, ion exchange chromatography, size-exclusion chromatography, HPLC or reverse phase HPLC, molecular sizing on a suitable Sephadex ® column, or the like. The final purification of the pre-purified product is achieved, for example, by means of affinity chromatography, for example antibody affinity chromatography, especially monoclonal antibody affinity chromatography using monoclonal anti-u-PA antibodies fixed on an insoluble matrix by methods known in the art, and the like. Advantageously, a detergent, especially a nonionic detergent, such as Triton X-100 ® or Tween 80 ®, is added to all buffer solutions used in the purification steps, in order to prevent the adsorption of the scu-PA protein to the vessel surfaces and to improve stability. The detergent may be added to a final concentration of 0.01–1%.

In the case where the scu-PA protein is secreted by the yeast cell into the periplasmic space, a simplified protocol can be used: The protein is recovered without cell lysis by enzymatic removal of the cell wall or by treatment with chemical agents, e.g. thiol reagents or EDTA, which gives rise to cell wall damages permitting the produced scu-PA protein to be released. In the case where the scu-PA protein is secreted into the culture broth, it can be recovered directly therefrom.

Dependent on the host strain used and the purification methods applied the scu-PA proteins according to the present invention may be contaminated with small amounts of the corresponding two chain forms caused by proteolytic activity released by the host cells. Separation of the two chain form from the desired one chain form (scu-PA) is accomplished by methods known in the art such as by chromatography on benzamidine-Sepharose ® [cf. M. E. Winkler et al. Biochemistry 25, 4041 (1986)].

Surprisingly, it was found that the scu-PA proteins according to the present invention differ from scu-PA obtained from *E. coli* in that they exhibit the biological activity of natural human scu-PA without any refolding procedure being necessary and in that they are yeast specifically glycosylated at Asn302. Owing to the yeast specific glycosylation the scu-PA proteins according to the invention are also distinct from scu-PA isolated from cultured or transformed animal cells and are thus novel.

Accordingly, the invention relates also to scu-PA and mutants thereof having yeast specific glycosylation, in particular having a glycosylation specific for *Saccharomyces cerevisiae*.

Mutants of scu-PA in which the glycosylation site is modified in such a way that glycosylation cannot take place at this site are likewise novel and are a further object of the present invention.

Accordingly, the invention concerns also compounds of the formula I in which $Z_1$ is the residue of a genetically encoded amino acid other than Asn, $Z_2$ is Thr and $X_1, X_2, Y_1, Y_2$ and $Y_3$ have the meanings given under formula I, and compounds of the formula I in which $Z_1$ is Asn, $Z_2$ is the residue of a genetically encoded amino acid other than Thr or Ser and $X_1, X_2, Y_1, Y_2$ and $Y_3$ have the meanings given under formula I.

In particular, the invention concerns compounds of the formula I in which $X_1$ is Lys, Gly or Ser, $X_2$ is Lys, $Y_1$ is Arg, $Y_2$ is Phe, Asp or Glu, $Y_3$ is Lys, $Z_1$ is Gln and $Z_2$ is Thr.

The most preferred compounds of the present invention are scu-PA, [Gly135]-scu-PA, [Ser135]-scu-PA, [Asp157]-scu-PA, [Ser135,Asp157]-scu-PA and [Gly135,Asp157]-scu-Pa wherein $Asn^{302}$ is yeast specifically glycosylated, and furthermore [Gln302]-scu-PA, [Gly135,Asp157,Gln302]-scu-PA and [Ser135,Asp157,Gln302]-scu-PA.

The transformed yeast strains according to the invention can be prepared by recombinant DNA techniques comprising the steps of
preparing a structural gene coding for scu-Pa or a mutant thereof,
incorporating the obtained structural gene into an appropriate vector,
transforming a suitable host organism with the produced hybrid vector and selecting transformed hosts from untransformed hosts.

The nucleotide sequences of u-PA cDNA and of genomic u-PA DNA are known [W. E. Holmes et al., Biotechnology 3, 923 (1985); A. Riccio et al. Nucleic Acids Research 13. 2759 (1985)]. Knowing the cDNA and genomic DNA sequences of u-PA the structural gene coding for u-PA or a mutant thereof can be made by methods known in the art. The methods for making these DNAs include isolating mRNA from human cells which produce scu-PA such as human carcinoma cells or human embryo kidney cells, selecting the desired mRNA, e.g. by hybridization with a suitable DNA probe, preparing single stranded DNA complementary to that mRNA, then double stranded complementary DNA (ds cDNA) therefrom, or isolating genomic DNA from human cells and selecting the desired DNA using a suitable DNA probe, and, if required, mutating the cDNA or genomic DNA obtained, or preparing the structural gene by chemical synthesis. Preferably, the structural genes according to the invention are prepared via the mRNA route and, if mutants are desired, by mutagenesis of the primarily obtained u-PA cDNA. Accordingly, the structural gene coding for a mutant of u-PA can be prepared by excising a portion of the DNA comprising the codon(s) for the undesired amino acid residue(s) from the parental mature u-PA gene and replacing it with a DNA segment wherein said codon(s) has (have) been substituted with codon(s) coding for the desired amino acid residue(s), or accomplishing the deoxyribonucleotide substitution by means of site directed mutagenesis [cf. M. J. Zoller et al. Methods Enzymol. 100, 468 (1983), D. Botstein et al. Science 229, 1193 (1985)].

The hybrid vectors according to the present invention comprise a yeast expression control sequence, a DNA segment consisting of a first DNA sequence encoding a signal peptide upstream of and in reading frame with a second DNA sequence coding for mature urokinase-type plasminogen activator or a mutant thereof, which DNA segment is under transcriptional control of said expression control sequence, and a DNA sequence comprising transcription termination signals of a yeast gene.

Yeast expression control sequences are derived from the genomic DNA of yeast, especially of pi Saccharomyces cerevisiae. Preferably, the expression control sequence of a highly expressed yeast gene is used for the expression of scu-PA. Thus, the promoter of the TRP1 gene, the ADHI or ADHII gene, acid phosphatase (PHO5) gene, a promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, or a promoter of the yeast mating pheromone genes coding for the a- or α-factor, can be used. It is also possible to use hybrid promoters comprising upstream activation sequences (UAS) of one yeast gene and downstream promoter elements including a functional TATA box of another yeast gene, for example a hybrid promoter including the UAS(s) of the yeast PHO5 gene and downstream promoter elements including a functional TATA box of the yeast GAPDH gene. Preferred vectors of the present invention contain promoters with transcriptional control. Promoters of this type, e.g. the promoter of the PHO5 gene and PHO5-GAPDH hybrid promoters, can be turned on or off by variation of the growth conditions. For example, the PHO5 promoter can be repressed at will, solely by increasing the concentration of inorganic phosphate in the medium. A further preferred promoter according to the invention is the promoter of the GAPDH gene, especially functional fragments thereof starting at nucleotides between -550 and -180, in particular at nucleotide -540, -263 or -198, and ending at nucleotide -5 of the GAPDH gene.

The DNA sequence encoding a signal peptide ("signal sequence") is preferably derived from eukaryotic, for example human or yeast, genes coding for polypeptides which are ordinarily secreted. Suitable signal sequences are, for example, the u-PA signal sequence obtainable from genomic human DNA, yeast signal sequences, such as the signal and prepro sequences of the yeast invertase, α-factor, pheromone peptidase (KEX1), "killer toxin" and repressible acid phosphatase (PHO5) genes and the glucoamylase signal sequence from *Aspergillus awamori*. Alternatively, fused signal sequences may be constructed by ligating part of the signal sequence (if present) of the gene naturally linked to the promoter used, with part of the u-PA signal sequence. Those combinations are favoured which allow a precise cleavage between the signal sequence and the mature scu-PA amino acid sequence. Additional sequences, such as pro- or spacersequences which may or may not carry specific processing signals can also be included in the constructions to facilitate accurate processing of precursor molecules. Alternatively fused proteins can be generated containing internal processing signals which allow proper maturation in vivo or in vitro. For example, the processing signals contain a Lys-Arg residue, which is recognized by a yeast endopeptidase located in the Golgi membranes. The preferred signal sequences according to the present invention are those of the yeast PHO5 gene coding for a signal peptide having the formula Met Phe Lys Ser Val Val Tyr Ser Ile Leu Ala Ala Ser Leu Ala Asn Ala, of the yeast invertase gene coding for a signal peptide having the formula Met Leu Leu Gln Ala Phe Leu Phe Leu Leu Ala Gly Phe Ala Ala Lys Ile Ser Ala.

and of the human u-PA gene coding for a signal peptide having the formula

Met Arg Ala Leu Leu Ala Arg Leu Leu Leu Cys Val Leu Val Val Ser Asp Ser Lys Gly.

A DNA sequence comprising yeast transcription termination signals is preferably the 3' flanking sequence of a yeast gene which contains proper signals for transcription termination and polyadenylation. Suitable 3' flanking sequences are for example those of the yeast gene naturally linked to the expression control sequence used. The preferred flanking sequences are those of the yeast PHO5 gene.

The hybrid plasmids according to the invention contain apart from the promoter, the signal sequence, the DNA sequence coding for u-PA or a mutant thereof and 3' flanking sequences additional DNA sequence(s) which perform important functions, for example, in the propagation of the cells transformed with said hybrid plasmids. The additional DNA sequence(s) may be derived from prokaryotic and/or eukaryotic cells and may include chromosomal and/or extra-chromosomal DNA sequences. For example, the additional DNA sequences may stem from (or consist of) plasmid DNA, such as bacterial or eukaryotic plasmid DNA, viral DNA and/or chromosomal DNA, such as bacterial, yeast or higher eukaryotic chromosomal DNA. Preferred hybrid plasmids contain additional DNA sequences derived from bacterial plasmids, especially *Escherichia coli* plasmid pBR322 or pUC19 related plasmids, bacteriophage λ, yeast 2μ plasmid, and/or yeast chromosomal DNA.

In the preferred hybrid plasmids according to the invention, the additional DNA sequences carry a yeast replication origin and a selective genetic marker for yeast. Hybrid plasmids containing a yeast replication origin, e.g. an autonomously replicating segment(ars), are extrachromosomally maintained within the yeast cell after transformation and are autonomously replicated upon mitosis. Hybrid plasmids containing sequences homologous to yeast 2μ plasmid DNA can be used as well. These hybrid plasmids recombine with the yeast 2μ plasmids already present within the cell or will replicate autonomously on their own if the origin of replication is present. 2μ sequences are especially suitable for high-frequency transformation plasmids and give rise to high copy numbers.

As to the selective gene marker for yeast, any marker gene can be used which facilitates the selection for transformants due to the phenotypic expression of the marker. Suitable dominant markers for yeast are particularly those expressing antibiotic resistance or, in the case of auxotrophic yeast mutants, genes which complement host lesions. Corresponding genes confer, for example, resistance to the antibiotic G418 or hygromycin or provide for prototrophy in an auxotrophic yeast mutant, for example the URA3, LEU2, HIS3 or TRP1 gene.

Advantageously, the additional DNA sequences which are present in the hybrid plasmids according to the invention also include a replication origin and a selective genetic marker for a bacterial host, especially *Escherichia coli*. There are useful features which are associated with the presence of an *E. coli* replication origin and an *E. coli* marker in a yeast hybrid plasmid. Firstly, large amounts of hybrid plasmid DNA can be obtained by growth and amplification in *E. coli* and, secondly, the construction of hybrid plasmids is conveniently done in *E. coli* making use of the whole repertoire of cloning technology based on *E. coli*. *E. coli* plasmids, such as pBR322 and the like, contain both *E. coli* replication origin and *E. coli* genetic markers conferring resistance to antibiotics, for example tetracycline and ampicillin, and are advantagously employed as part of the yeast hybrid vectors.

The additional DNA sequences which contain, for example, replication origin and genetic markers for yeast and a bacterial host (see above) are hereinafter referred to as "vector DNA" which together with the yeast promoter and the scu-PA protein coding region is forming a hybrid plasmid according to the invention.

In a preferred embodiment, the present invention relates to hybrid plasmids capable of autonomous replication in a yeast host strain and having selectable markers comprising a yeast expression control sequence, a DNA segment consisting of a first DNA sequence encoding a signal peptide upstream of and in reading frame with a second DNA sequence coding for mature urokinase-type plasminogen activator or a mutant thereof, and a DNA sequence containing transcription termination signals of a yeast gene, said DNA segment being positioned together with transcription start and termination signals as well as encoded translation start and stop signals in said hybrid vector under control of said expression control sequence such that in a transformed yeast strain it is expressed to produce said urokinase-type plasminogen activator or mutants thereof.

The hybrid vectors of the present invention are prepared by methods known in the art, for example by linking a yeast expression control sequence, a DNA segment consisting of the signal peptide coding region and a DNA sequence coding for u-PA or a mutant thereof, the 3' flanking sequence of a yeast gene and vector DNA.

For the preparation of hybrid plasmids, conveniently mapped circular vector DNA, for example bacterial plasmid DNA or the like (see above), having at least one restriction site, preferably two or more restriction sites, can be employed. Advantageously, the vector DNA already contains replication origins and gene markers for yeast and/or a bacterial host. The vector DNA is cleaved using an appropriate restriction endonuclease. The restricted DNA is ligated to the DNA fragment(s) containing the yeast expression control sequence, said DNA segment and said DNA sequence containing transcription termination signals. Prior to or after linking of said DNA fragment(s) (or simultaneously as well), it is also possible to introduce replication origins and/or markers for yeast or a bacterial host. At all events, the restriction and ligation conditions are to be chosen in such a manner that there is no interference with the essential functions of the vector DNA and of the expression control sequence. The hybrid vector may be built up sequentially or by ligating two DNA segments comprising all sequences of interest.

Various techniques may be used to join DNA segments in vitro. Blunt ends (fully base-paired DNA duplexes) produced by certain restriction endonucleases may be directly ligated with T4 DNA ligase. More usually, DNA segments are linked through their single-stranded cohesive ends and covalently closed by a DNA ligase, e.g. T4 DNA ligase. Such single-stranded "cohesive termini" may be formed by cleaving DNA with another class of endonucleases which produce staggered ends (the two strands of the DNA duplex are cleaved at different points at a distance of a few nucleotides). Single strands can also be formed by the addition of nucleotides to blunt ends or staggered ends using terminal transferase ("homopolymeric tailing") or by simply chewing back one strand of a blunt-ended DNA segment with a suitable exonuclease, such as λ exonuclease. A further approach to the production of staggered ends consists in ligating to the blunt-ended DNA segment a chemically synthesized linker DNA which contains a recognition site for a staggered-end forming endonuclease and digesting the resulting DNA with the respective endonuclease.

The components of the hybrid vector according to the invention, such as the yeast promoter, structural gene for u-PA or a mutant thereof including a signal sequence, transcription terminator, the replication system etc., are linked together in a predetermined order to assure proper function. The components are linked through common restriction sites or by means of synthetic linker molecules to assure proper orientation and order of the components.

The transformed yeast strains according to the invention are made in a manner known per se, viz. transforming a yeast strain with a hybrid vector comprising a yeast expression control sequence, a DNA segment consisting of a first DNA sequence encoding a signal peptide upstream of and in reading frame with a second DNA sequence coding for mature urokinase-type plasminogen activator or a mutant thereof, which DNA segment is under transcriptional control of said expression control sequence, and a DNA sequence containing transcription termination signals of a yeast gene.

Suitable yeast host organisms include species of the genera *Kluyveromyces, Candida, Pichia, Saccharomyces, Yarrowia, Torulopsis* and related genera (cf. J. Lodder, The Yeasts, Amsterdam 1971), especially strains of *Saccharomyces cerevisiae.*

The transformation of the yeast host cells is accomplished by methods known in the art. For example, the transformation may be accomplished according to the method described by Hinnen et al [Proc. Natl. Acad. Sci. USA 75. 1929(1978)]. This method can be divided into three steps:

(1) Removal of the yeast cell wall or parts thereof.
(2) Treatment of the "naked" yeast cells (spheroplasts) with the transforming DNA in the presence of PEG (polyethyleneglycol) and $Ca^{2+}$ ions.
(3) Regeneration of the cell wall and selection of the transformed cells in a solid layer of agar.

Preferred methods:

ad (1): The yeast cell wall is removed enzymatically using various preparations of glucosidases, such as snail gut juices (e.g. Glusulase ® or Helicase ®) or enzyme mixtures obtained from microorganisms (e.g. Zymolyase ®) in osmotically stabilized solutions (e.g. 1 M sorbitol).

ad (2): The yeast spheroplasts aggregate in the presence of PEG and local fusions of the cytoplasmic membranes are induced. The generation of "fusion-like" conditions is crucial and many transformed yeast cells become diploid or even triploid during the process of transformation. Procedures which allow selection of fused spheroplasts can be used to enrich for transformants, i.e. transformed cells can easily be screened for among preselected fusion products.

ad (3): Since yeast cells without cell wall do not divide the cell wall has to be regenerated. This regeneration is conveniently done by embedding the spheroplasts into agar. For example, molten agar (about 50° C.) is mixed with the spheroplasts. Upon cooling the solution to yeast growth temperatures (about 30° C.), a solid layer is obtained. This agar layer is to prevent rapid diffusion and loss of essential macromolecules from the spheroplasts and thereby facilitates regeneration of the cell wall. However, cell wall regeneration may also be obtained (although at lower efficiency) by plating the spheroplasts onto the surface of preformed agar layers.

Preferably, the regeneration agar is prepared in a way to allow regeneration and selection of transformed cells at the same time. Since yeast genes coding for enzymes of amino acid biosynthetic pathways are generally used as selective markers (supra), the regeneration is preferably performed in yeast minimal medium agar. If very high efficiencies of regeneration are required the following two step procedure is advantageous: (1) regeneration of the cell wall in a rich complex medium, and (2) selection of the transformed cells by replica plating the cell layer onto selective agar plates.

If the hybrid vector does not contain any marker gene the transformed cells can also be identified by means of alternative methods. Such methods include, for example, in situ hybridization with a labeled DNA fragment homologous to sequences of the hybrid vector [e.g. according to Hinnen et al., supra], in situ immunoassays provided that an antibody for the product of the introduced gene is available, or other screening methods which measure gene products encoded by the transforming plasmid(s).

Alternatively, the yeast can be co-transformed with a hybrid vector according to the invention and a second vector containing a genetic marker for yeast. If the two different vectors have DNA sequences in common (these can be bacterial sequences), recombination takes place leading to a fused selectable hybrid molecule.

The transformed yeast strains containing the hybrid plasmids according to the invention can be improved in production of scu-PA or mutants thereof by mutation and selection using methods known in the art. The mutation can be effected, for example, by U.V. irradiation or suitable chemical reagents. Especially preferred is the production of protease deficient mutants, especially yeast mutants, so as to avoid proteolytic degradation of the produced scu-PA or mutants thereof within the cells. Suitable mutants can be selected and isolated by conventional means.

The scu-PA proteins, obtainable according to the present invention, especially the novel scu-PA proteins, exhibit valuable pharmacological properties. They can be used in analogy to known plasminogen activators in humans for the prevention or treatment of thrombosis or other conditions where it is desired to produce local fibrinolytic or proteolytic activity via the mechanism of plasminogen activation, such as arteriosclerosis, myocardial and cerebral infarction, venous thrombosis, thromboembolism, post-surgical thrombosis, thrombophlebitis and diabetic vasculopathies.

The invention relates also to pharmaceutical compositions that contain a therapeutically effective amount of the active ingredient (scu-PA or a mutant thereof) together with organic or inorganic, solid or liquid pharmaceutically acceptable carriers that are suitable for parenteral, such as intravenous, administration and that do not deleteriously interact with the active ingredients.

There are suitable especially infusion solutions, preferably aqueous solutions or suspensions, it being possible to prepare these before use, for example from lyophilised preparations that contain the active ingredient alone or together with a carrier, such as mannitol, lactose, glucose, albumin and the like. The pharmaceutical composition may be sterilized and, if desired, mixed with adjuncts, for example preservatives, stabilisers, emulsifiers, solubilisers, buffers and/or salts, such as sodium chloride, for regulating the osmotic pressure. Sterilization can be achieved by sterile filtration through filters of small pore size (0.45 μm diameter or smaller) after which the preparation can be lyophilised, if desired. Antibiotics may also be added in order to assist in preserving sterility. For example, the scu-PA protein according to the invention is formulated into a sterilized aqeuous solution containing 5% glucose and optionally stabilisers and salts.

The pharmaceutical compositions according to the present invention are dispensed in unit dosage forms, for example ampoules, comprising 1 to 2000 mg of a pharmaceutically acceptable carrier per unit dosage and about 1 to 20 mg, preferably about 3 to 15 mg, of the active ingredient (scu-PA or a mutant thereof) per unit dosage.

Depending upon the type of the disease and the age and the condition of the patient, the daily dose to be administered for the treatment of a patient weighing approximately 70 kg is in the range from 20 to 150 mg, preferably from 45 to 100 mg, per 24 hours.

The invention also concerns a method for producing a pharmaceutical composition characterised in that a biologically active protein of the present invention is admixed with a pharmaceutically acceptable carrier.

The use of the new proteins for the prophylactic and therapeutic treatment of the human body is also an object of the present invention.

The invention concerns also the novel hybrid plasmids and the yeast strains transformed with said hybrid plasmids and the processes for the production thereof.

The invention relates especially to the scu-PA proteins, hybrid vectors, transformed yeast hosts and to the processes for the production thereof as described in the Examples.

BRIEF DESCRIPTION OF THE DRAWINGS

In the following experimental part various embodiments of the present invention are described with reference to the accompanying drawings in which:

FIG. 2 illustrates the nucleotide sequence and deduced amino acid sequence of human u-PA cDNA. The first amino acid of the mature protein is underlined.

FIG. 3 schematically illustrates the construction of plasmid pCS16.

FIG. 6 provides the DNA sequence of the promoter region of GAPDH.

FIG. 8 depicts promoter elements of the GAPDH gene used in the present invention.

FIG. 13 provides the DNA sequences of the mutated u-PA genes and the corresponding amino acid sequences of the mutant scu-PA proteins according to the invention.

The following Examples serve to illustrate the present invention but should not be construed as a limitation thereof.

EXPERIMENTAL PART

Example 1

Construction of plasmid pCS16/UPA comprising the u-PA coding region

A) Construction of plasmid pCS16 (see FIG. 3)

A 1.5 kb PstI-BamHI fragment of plasmid pUN121 [B. Nilsson et al. Nucl. Acids Res. 11, 8019–8030 (1983)] comprising the cI gene of phage lambda and part of the tetracyclin resistance gene is cloned into pUC18 [J. Norrander et al., Gene 26, 101–106 (1983)], cut with Pst1 and BamHI. The resulting clone is digested with PstI. The 3' overhanging ends are removed in a reaction with $T_4$ DNA polymerase [T. Maniatis et al., Molecular Cloning (1982), p. 395] and XhoI linkers (5'-CCTCGAGG-3', Biolabs) are ligated to the blunt ends. After digestion with XhoI the molecule is recircularised by ligation. An aliquot of the ligation mixture is used to transform $Ca^{++}$ treated E. coli HB101 cells. The DNA of individual ampicillin resistant, transformed colonies is analysed. One of several correct clones is chosen and referred to as pCS16.

Figure 4:
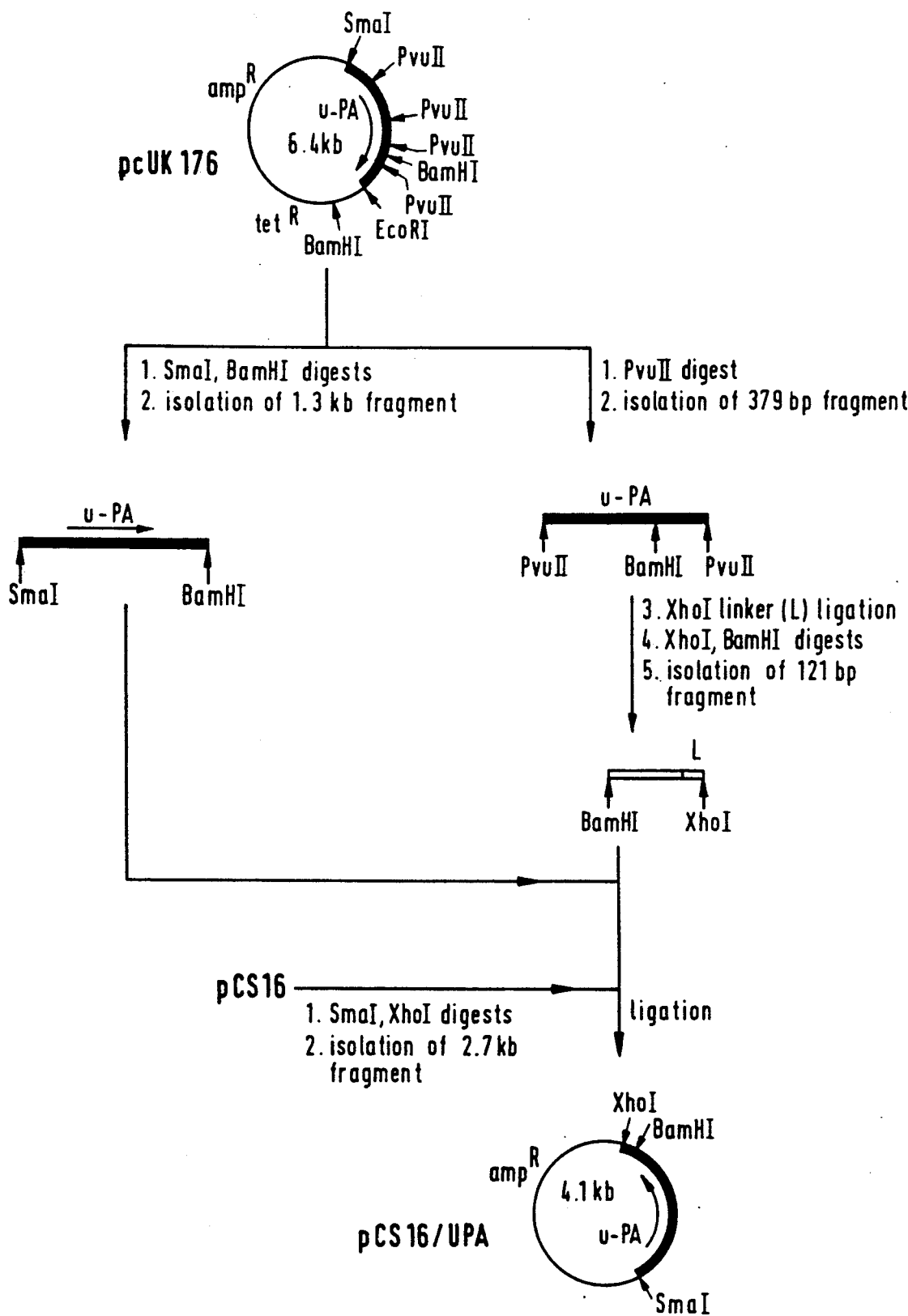
FIG. 4 schematically illustrates the construction of plasmid pCS16/UPA comprising the u-PA cDNA.

B) Construction of plasmid pCS16/UPA (see FIG. 4)

Figure 1:
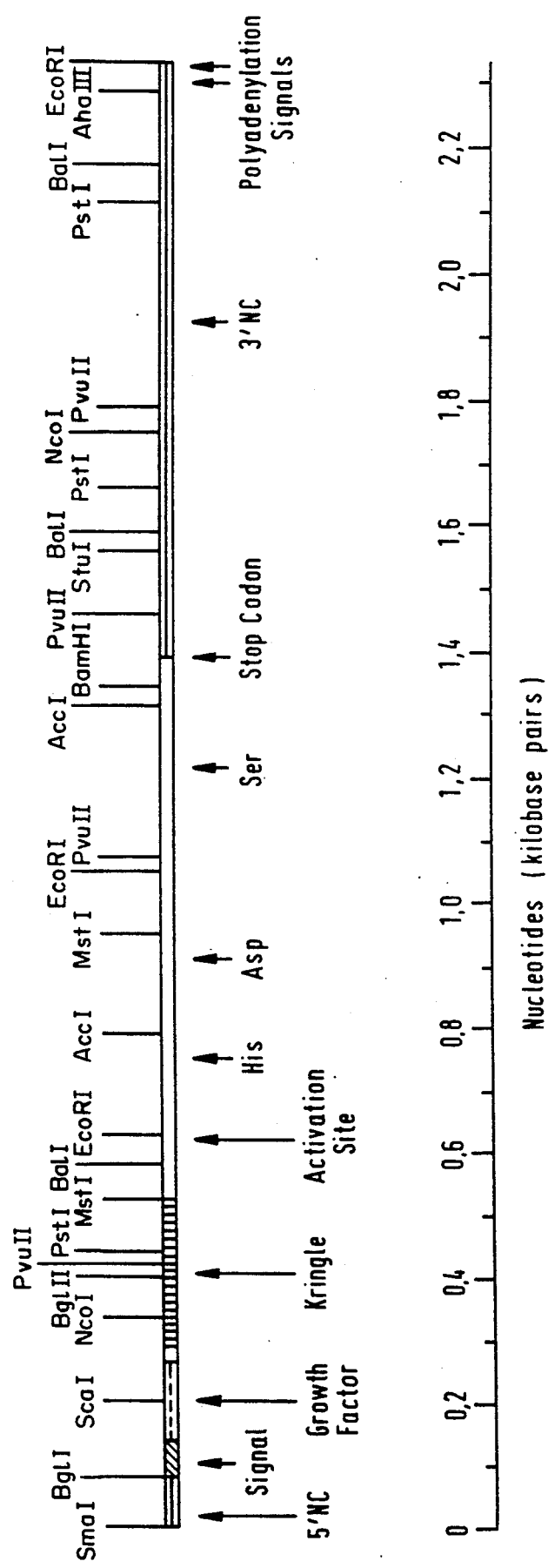
FIG. 1 is a restriction endonuclease map of human u-PA cDNA.

Urokinase cDNA is prepared from mRNA obtained from human Hep3 cells [cf. T. Maniatis et al., p. 188–246, supra]. A 1.3 kb SmaI-BamHI fragment and a 1 kb BamHI-EcoRI fragment of the u-PA cDNA is cloned into the SmaI, EcoRI sites of pUN121 [B. Nilsson et al., Nucl. Acids Res. 11, 8019–8030 (1983)] to yield plasmid pcUK176. The restriction endonuclease map of the human u-PA cDNA insert is shown in FIG. 1. The nucleotide sequence and deduced amino acid sequence of the u-PA insert is given in FIG. 2. The u-PA cDNA insert is subcloned in plasmid pCS16. The subcloned cDNA extends from the SmaI site in the 5' nontranslated region (FIG. 1) to the PvuII site at nucleotide positions 1439–1444 (FIG. 2) in the 3' nontranslated region.

15 μg of plasmid pcUK176 are digested with PvuII. The 379 bp PvuII fragment is separated from other fragments on a 1.5% agarose gel in Tris-borate-EDTA buffer pH 8.3. The DNA is electroeluted, purified by DE52 (Whatman) ion exchange chromatography and precipitated by ethanol. 1.2 μg of single stranded XhoI linkers (5'-CCTCGAGG-3') are phosphorylated at their 5' ends, heated for 10 min at 75° C., self annealed during cooling to room temperature and stored at −20° C. 0.9 μg of the kinased, double stranded XhoI linkers are ligated at an 80-fold molar excess to the blunt ends of the 379 bp PvuII fragment of pcUK176 (see above) in 20 μl of 60 mM Tris-HCl pH 7.5, 10 mM $MgCl_2$, 5 mM DTT, 3.5 mM ATP and 400 units of $T_4$ DNA ligase (Biolabs) at 15° C. for 16 hours. The mixture is heated for 10 min at 85° C. Excess linker molecules are removed by precipitation with 0.54 volumes of isopropanol in the presence of 10 mM EDTA and 300 mM sodium acetate pH 6.0 for 30 min at room temperature. The DNA is digested with XhoI and BamHI. A 121 bp BamHI-XhoI fragment is isolated on a 1.5% agarose gel in Tris-borate-EDTA buffer pH 8.3. 6 μg of plasmid pcUK176 are digested with SmaI and BamHI. A 1.3 kb SmaI-BamHI fragment comprising most of the u-PA coding sequence is isolated. 6 μg of plasmid pCS16 are digested with SmaI and XhoI. The 2.7 kb vector fragment is isolated. The DNA fragments are electroeluted from the gel and ethanol precipitated. 0.2 pmoles of the 1.3 kb SmaI-BamHI fragment, 0.2 pmoles of the 121 bp BamHI-XhoI fragment (both fragments together comprise the full u-PA coding sequence) and 0.1 pmoles of the 2.7 kb vector fragment are ligated in 10 μl of 60 mM Tris.HCl pH 7.5, 10 mM MgCl$_2$, 5 mM DTT, 3.5 mM ATP and 400 units of T$_4$ DNA ligase at 15° C. One and 3 μl aliquots of the ligation mixture are added to 100 pl of Ca$^{++}$ treated E. coli HB101 cells. Transformation is carried out as described [A. Hinnen et. al., Proc.Natl. Acad. Sci. USA 75. 1929 (1978)]. 12 ampicillin resistant colonies are grown in LB medium containing 100 mg/l ampicillin. DNA is isolated according to Holmes et al. [Anal. Biochem. 114, 193 (1981)] and analysed by EcoRI, PvuII and XhoI restriction digests. Plasmid DNA of a single clone with the expected restriction fragments is referred to as pCS16/UPA.

In an analogous manner the urokinase cDNA from the SmaI site (nucleotide positions 1-6, FIG. 2) to the PstI site at nucleotide positions 1637-1642 (see FIG. 2) is subcloned in plasmid pCS16. Plasmid pcUK176 is digested with PstI. The sticky ends are converted to blunt ends in a reaction with T4 DNA polymerase as described by Maniatis et al. (supra, p. 395). The 1.2 kb DNA fragment is isolated. XhoI linkers are added as described above. The DNA is digested with BamHI and XhoI and a 315 bp BamHI-XhoI fragment is isolated. 0.2 pmoles of this fragment are ligated to the 1.3 kb SmaI-BamHI fragment and the 2.7 kb vector fragment (see above). The ligation mixture is used to transform E. coli HB101 Ca$^{++}$ cells. Plasmid DNA of a single clone with the expected restriction fragments is referred to as pCS16/UPA-13. This plasmid contains the u-PA cDNA insert from the SmaI site in the 5' nontranslated region (FIG. 1) to the PstI site at nucleotide position 1641 (FIG. 2) in the 3' nontranslated region. The only difference to plasmid pCS16/UPA is the extended 3' nontranslated region.

Example 2

Construction of plasmid p31RIT-12 containing the PH05 promoter and the invertase signal sequence A) Synthesis of oligodeoxyribonucleotides for invertase signal sequence:

Four oligodeoxyribonuclotides: I-1, I-2, I-3, I-4 are synthesized by DNA synthesizer (model 380B Applied Biosystems). After deblocking the synthetic fragments are purified on a 12% polyacrylamide gel containing 8 M urea. Salt-free pure oligodeoxyribonucleotides are obtained using Sep. Pak (Waters Associates). These fragments constitute a duplex which encodes the invertase signal sequence with the frequently used yeast codons.

MgCl$_2$, 100 mM NaCl, 6 mM mercaptoethanol for one hour at 37° C. After adding 1 μl of 2.5 M NaCl, 10 U of XhoI (Boehringer) are added and incubated at 37° C. for one hour. The 4.2 kb vector is isolated on a 0.8% preparative agarose gel. The gel slice is transferred to a Micro Colloidor tube (Sartorius GmbH), covered with 200 μl of TE and electroeluted (electrophoresed at 90 mA for 50 min). The TE solution is collected and precipitated in 2.5 volumes of absolute ethanol after the addition of 0.1 volume 10×TNE. The DNA pellet is washed with cold 80% ethanol and dried in vacuum. The DNA is resuspended in 6 μl TE (40 pmoles/μl).

b) Annealing oligodeoxyribonucleotides (I-1, I-2, I-3, I-4), kination and ligation with vector A solution containing 10 pmoles of each of the four deoxyribonucleotides in 10 μl of 0.5 M Tris.HCl pH 8 is incubated at 95° C. for 5 minutes on a water bath. The water bath is slowly cooled to 30° C. over a period of 5 hours. To this annealed mixture is added 2 μl each of 0.1 M MgCl$_2$, 0.1 M NaCl, 30 mM DTT, 4 mM ATP and 8 U (1 μl) of polynucleotide kinase (Boehringer). Kination is carried out at 37° C. for one hour. The annealed, kinased oligodeoxyribonucleotides and 60 pmoles of p31R/SS-TPAA2 EcoRI-XhoI cut vector (1.5 μl) are ligated with 400 U (1 μl) of T4 DNA ligase (Biolabs) at 14° C. for 17 hours. The reaction is stopped by incubation at 65° C. for 10 min. 10 μl of this ligation mixture is used for transformation of E. coli HB101 Ca$^{++}$ cells [M. Dagert and S. D. Ehrlich, Gene 56. 23-28 (1979)]. 20 amp$^R$ colonies are picked. DNA is prepared by the quick isolation procedure [D. S. Holmes and M. Quigley, Anal. Biochem. 114, 193-197 (1981)]. DNA is digested with EcoRI and XhoI, radiolabelled at the EcoRI end and analysed on a 6% polyacryalmide gel containing 8 M urea using radiolabelled pBR322 HaeIII cut DNA as marker. Correct size bands are observed for DNA obtained from all the 20 clones. One clone is grown in 100 ml LB medium containing 100 μg/ml of ampicillin. Plasmid DNA is isolated and is referred to as p31RIT-12.

Example 3

Figure 5:
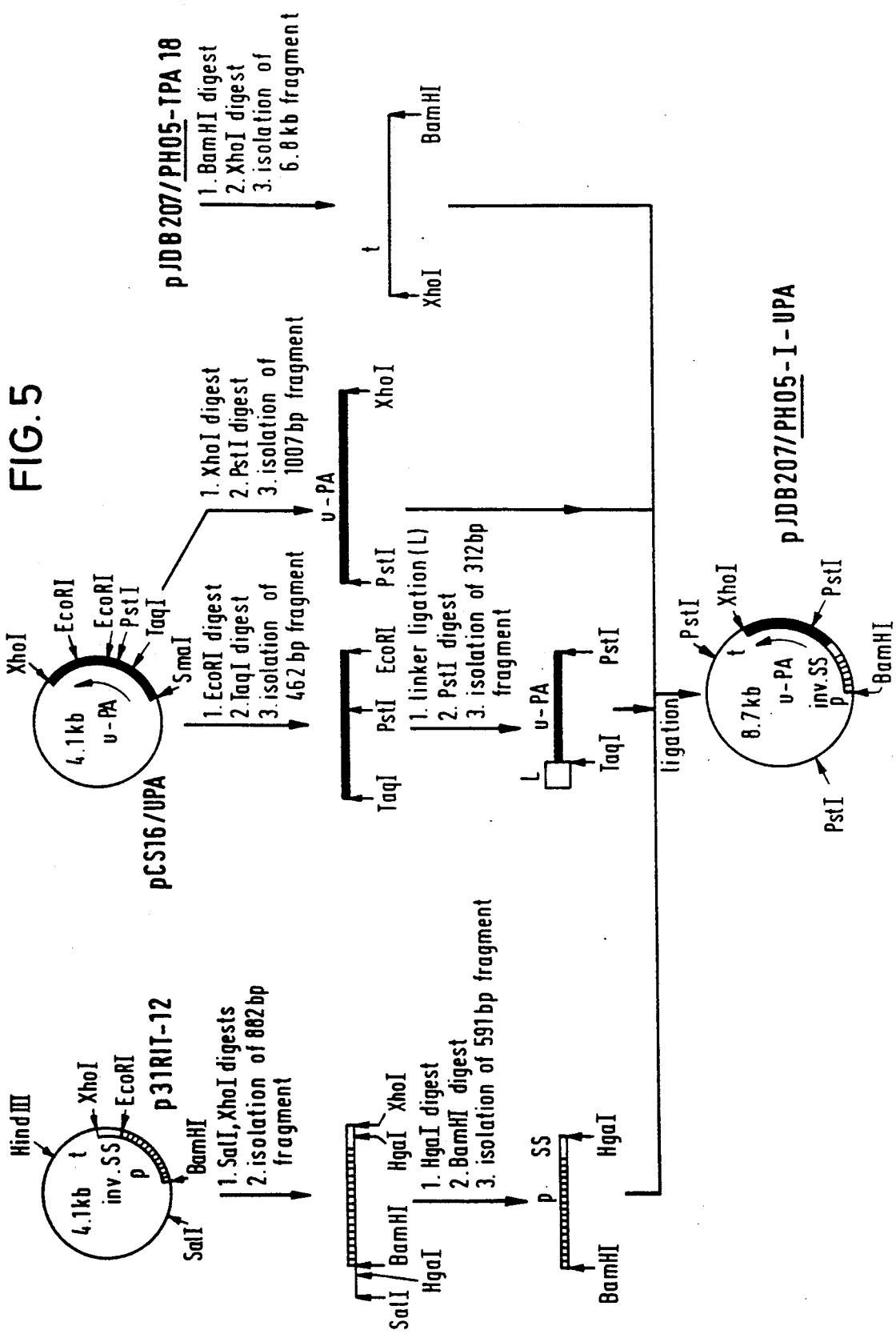
FIG. 5 is a schematic diagram showing the construction of plasmid pJDB207/PH05-I-UPA (abbreviations used: SS signal sequence; t transcription terminator; p promoter; L linker).

Construction of plasmid pJDB207/PH05-I-UPA (FIG. 5)

pJDB207/PH05-I-UPA contains the PH05 promoter, the invertase signal sequence, the coding sequence of mature urokinase and the PH05 transcription terminator in a tandem array cloned into the pJDB207 yeast expression vector.

20 μg of plasmid pCS16/UPA are digested to completion with 40 units of EcoRI. After phenol extraction and ethanol precipitation the EcoRI digested DNA is further cut by TaqI at 65° C. The resulting fragments are separated on a preparative 1.2% agarose gel. The 462 bp TaqI-EcoRI fragment is isolated by electroelution from the gel and ethanol precipitation.

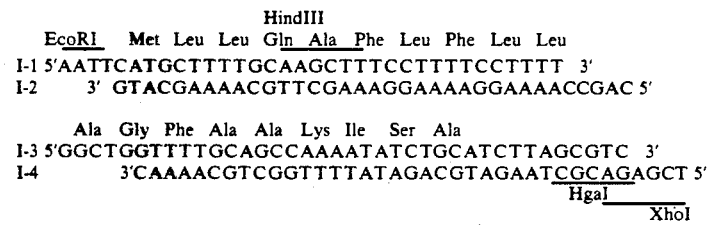

```
                              HindIII
      EcoRI   Met Leu Leu Gln Ala Phe Leu Phe Leu Leu
I-1 5'AATTCATGCTTTTGCAAGCTTTCCTTTTCCTTTT 3'
I-2     3' GTACGAAAACGTTCGAAAGGAAAAGGAAAACCGAC 5'

Ala Gly Phe Ala Ala Lys Ile Ser Ala
I-3 5'GGCTGGTTTTGCAGCCAAAATATCTGCATCTTAGCGTC 3'
I-4     3'CAAAACGTCGGTTTTATAGACGTAGAATCGCAGAGCT 5'
                                       HgaI
                                           XhoI
```

B) Subcloning of the invertase signal sequence in plasmid p31 a) preparation of vector:
1.5 μg of p31R/SS-TPAA2 (European Patent Application No. 143,081) is digested with 10 U of EcoRI (Boehringer) in 50 μl of 10 mM Tris.HCl pH 7.5, 6 mM An oligodesoxyribonucleotide linker of the formula

5'-CTGCAAGCAATGAACTTCATCAAGTT-CCAT-3'  (I)

3'-TCGTTACTTGAAGTAGTTCAAGGTAGC-5'  (II)

is ligated to the TaqI site of the DNA fragment. The linker restores the 5' terminus of the coding sequence of mature u-PA (nucleotides 130-154, FIG. 2) and establishes the in frame fusion to the invertase signal sequence. The 5'-CTGCA sequence of the linker fills the corresponding 3' recessed end of the invertase signal sequence created by HgaI cleavage.

300 pmoles each of the oligodesoxynucleotides I and II are phosphorylated and annealed. 5.25 μg (600 pmoles) of phosphorylated, double-stranded linker DNA are ligated to 1.7 μg (5.6 pmoles) of the 462 bp TaqI-EcoRI fragment (see above) in 175 μl of 60 mM Tris-HCl pH 7 5, 10 mM MgCl₂, 1 mM ATP, 5 mM DTT and 800 units of T4 DNA ligase at 15° C. for 16 hours. T4 DNA ligase is inactivated for 10 min at 85° C. The excess of linkers is removed by precipitation in the presence of 10 mM EDTA, 300 mM sodium acetate pH 6.0 and 0.54 volumes of isopropanol. The DNA is digested with PstI. An unique 312 bp fragment is isolated containing the linker attached to DNA sequences coding for u-PA up to nucleotide 436 (PstI site, see FIG. 2). The DNA fragment is purified by electroelution and precipitation with ethanol.

Plasmid pCS16/UPA is digested with XhoI and PstI. A 1007 bp PstI-XhoI fragment is isolated and purified. This fragment contains most of the coding sequence for urokinase.

Plasmid p31RIT-12 (see Example 2) is digested with SalI and XhoI. An 882 bp SalI-XhoI fragment is isolated from the gel by electroelution and ethanol precipitation. The fragment is further digested with BamHI and HgaI. A 591 bp BamHI-HgaI fragment is isolated which contains the PH05 promoter region and the invertase signal sequence.

Plasmid pJDB207/PH05-TPA 18 (see European Patent Application No. 143,081) is digested with BamHI and XhoI. The 6.8 kb vector fragment is isolated on a preparative 0.6% agarose gel in Trisacetate buffer pH 8.2. The DNA is electroeluted and precipitated with ethanol.

All DNA fragments are resuspended in H₂O at a concentration of 0.1 pmoles/μl. 0.2 pmoles of the 591 bp BamHI-HgaI fragment, 0.2 pmoles of the 312 bp HgaI-PstI fragment, 0.2 pmoles of the 1007 bp PstI-XhoI fragment and 0.1 pmoles of the 6.8 kb BamHI-XhoI vector fragment are ligated for 15 h at 15° C. in 10 μl of 50 mM Tris.HCl pH 7.5, 10 mM MgCl₂, 5 mM DTT, 1 mM ATP and 400 units of T4 DNA ligase. One μl of the ligation mixture is used to transform E. coli HB101 Ca++ cells. 12 amp$^R$ colonies are picked and grown in LB medium containing 100 mg/l of ampicillin. DNA is prepared by the quick isolation procedure [D. S. Holmes et al., Anal. Biochem. 114, 193 (1981)]. On restriction digests of the plasmid DNA with HindIII and EcoRI the expected restriction fragments are observed. Plasmid DNA of a single clone is selected and referred to as pJDB207/PH05-I-UPA.

Example 4

Construction of plasmid pJDB207/PH05-UPA

This construction comprises the PH05 promoter, the PH05 signal sequence joined in frame to the coding sequence of mature urokinase and the PH05 transcription terminator cloned into the pJDB207 yeast vector.

An oligodesoxyribonucleotide linker of the formula

5'-CCAATGCAAGCAATGAACTTCAT-CAAGTTCCAT-3'  (I)

3'-GGTTACGTTCGTTACTTGAAGTAGTT-CAAGGTAGC-5'  (II)

provides 8 nucleotides (5'-CCAATGCA) of the PH05 signal sequence (from an internal BalI site to its processing site) and establishes an in frame fusion to the coding sequence of mature u-PA (nucleotide positions 130-154, FIG. 2). The linker is ligated to the TaqI site of the 462 bp TaqI-EcoRI fragment of pCS16/UPA (see Example 3). Phosphorylation, annealing and ligation is done according to Example 3. The DNA is digested with BalI and PstI. A 315 bp fragment is isolated. The DNA fragment contains the DNA sequence of the u-PA gene up to the PstI site at position 436 (FIG. 2).

Plasmid p31 (see European Patent Application No. 100,561) is digested with BalI and BamHI. A 584 bp BamHI-BalI fragment is isolated containing the PH05 promoter and most of the PH05 signal sequence. The DNA fragments are purified by electroelution and DE52 chromatography, precipitated with ethanol and resuspended in H₂O at a concentration of 0.1 pmoles/μl.

0.2 pmoles of the 584 bp BamHI-BalI fragment, 0.2 pmoles of the 315 bp BalI-PstI fragment, 0.2 pmoles of the 1007 bp PstI-XhoI fragment (see Example 3) and 0.1 pmoles of the 6.8 kb BamHI-XhoI vector fragment (see Example 3) are ligated and used to transform E. coli HB101. 6 amp$^R$ colonies are picked and grown in LB medium containing 100 mg/l of ampicillin. Plasmid DNA is prepared by the quick DNA procedure and analysed by BamHI/PstI double digestion. A single clone with the expected restriction fragments is selected and the plasmid DNA is referred to as pJDB207/PH05-UPA.

Example 5

Construction of plasmid pJDB207/PH05-SSUPA

This plasmid contains the urokinase gene with its own signal sequence under the control of the PH05 promoter in the yeast expression vector pJDB207.

20 μg of plasmid pCS16/UPA-13 (see Example 1) are digested to completion with 100 units of BglI (nucleotide positions 76-86, FIG. 2). The resulting 3 fragments are separated on a preparative 1% agarose gel in Tris-borate-EDTA buffer pH 8.3. The 1.7 kb BglI fragment is electroeluted and precipitated with ethanol.

An oligodesoxyribonucleotide linker of the formula

5'-AATTCGATTACCAATGAGAGCCCTGC-3'  (I)

3'-GCTAATGGTTACTCTCGGG-5'  (II)

has an EcoRI site linked to 8 nucleotides of the PH05 5' noncoding region in front of its ATG and nucleotides 70-82 (FIG. 2) of the coding sequence of u-PA including the ATG. The linker is ligated to the BglI sticky ends of DNA as described in Example 3. The DNA is digested with EcoRI and PstI.

A 380 bp fragment is isolated comprising the u-PA signal sequence and part of the coding sequence for mature u-PA up to nucleotide 436 (PstI site, FIG. 2).

Plasmid p31R (see European Patent Application No. 100,561) is digested with BamHI and EcoRI and the 534 bp BamHI-EcoRI fragment is isolated comprising the PH05 promoter. DNA fragments are electroeluted from the agarose gel, purified by DE52 chromatography, precipitated with ethanol and resuspended in $H_2O$ at a concentration of 0.1 pmoles/$\mu$l.

0.2 pmoles of the 534 bp BamHI-EcoRI fragment, 0.2 pmoles of the 380 bp EcoRI-PstI fragment, 0.2 pmoles of the 1007 bp PstI-XhoI fragment (see Example 3) and 0.1 pmoles of the 6.8 kb BamHI-XhoI vector fragment (see Example 3) are ligated and used to transform E. coli HB101 Ca++ cells. 12 amp$^R$ colonies are grown separately in LB medium containing 100 mg/l of ampicillin. DNA is prepared by the quick DNA procedure and analysed by BamHI and EcoRI. Plasmid DNA from a single clone is selected and referred to as pJDB207/PH05-SSUPA.

Example 6

Construction of plasmid pJDB207R/PH05-UPA

The coding sequence of mature urokinase is linked to the PH05 promoter. No signal sequence is included in this construct which has been made for comparative purposes.

An oligodesoxyribonucleotide linker of the formula

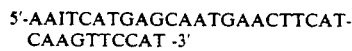

contains an ATG and nucleotides 130-154 of u-PA (see FIG. 1) coding for amino acids Ser1 to Ser9 of mature urokinase. The oligonucleotides are phosphorylated, annealed and ligated to the 462 bp TaqI-EcoRI fragment of pCS16/UPA (see Example 3). The DNA is digested with EcoRI and PstI. A 315 bp EcoRI-PstI fragment is isolated comprising the ATG and the coding sequence for mature u-PA up to the PstI site at position 436 (FIG. 2).

Plasmid p31R (see European Patent Application No. 100,561) is digested with BamHI and EcoRI and the 534 bp BamHI-EcoRI fragment is isolated on a preparative 1.5% agarose gel. This fragment contains the PH05 promoter.

All DNA fragments are electroeluted, purified by DE52 chromatography, precipitated with ethanol and resuspended in $H_2O$ at a concentration of 0.1 pmoles/$\mu$l. 0.2 pmoles each of the 534 bp BamHI-EcoRI fragment, the 315 bp EcoRI-PstI fragment and the 1007 bp PstI-XhoI fragment (see Example 3) and 0.1 pmoles of the 6.8 kb BamHI-XhoI vector fragment (see Example 3) are ligated and transformed into E. coli HB101 Ca++ as usual. 8 amp$^R$ colonies are picked and grown in LB medium containing 100 mg/l of ampicillin. Plasmid DNA is prepared and analysed by BamHI and EcoRI restriction digests. Plasmid DNA of a single clone with the expected restriction pattern is referred to as pJDB207R/PH05-UPA.

Example 7

Cloning of the yeast GAPDH gene with its constitutive promoter a) Construction of a yeast gene library Thirty $\mu$g of total high molecular weight yeast DNA [M. V. Olsen et al. J. Mol.Biol. 132, 387 (1979)] form wild type Saccharomyces cerevisiae strain S288C is incubated for 30 min at 37° C. with 2 units of EcoRI methylase (New England Biolabs) in 250 $\mu$l of EcoRI methylation buffer as recommended by the supplier. DNA is precipitated by ethanol, resuspended in 500 $\mu$l of 25 mM Tris.HCl pH 8.5, 2 mM $MgCl_2$ (EcoRI* buffer) [H. Meyer, FEBS Lett. 90, 341 (1979)] and digested with EcoRI (Boehringer) until the size distribution of the DNA fragments has a maximum in the 30-50 kb range (a XhoI digest of $\lambda$DNA provides appropriate 33 kb and 17 kb markers). The yeast DNA digested under EcoRI* conditions is size-fractionated on a sucrose gradient (5-20% sucrose in 10 mM Tris.HCl pH 7.5, 1 mM EDTA) for 6 hrs at 38000 rpm in a SW 40 rotor. Thirty fractions of 0.4 ml each are collected from the top of the gradient. Fraction 16 contains DNA fragments of 30-40 kb in size. The DNA of this fraction (3 $\mu$g) is precipitated with ethanol and ligated for 16 hours at 15°0 C. in a total volume of 15 $\mu$l to 1 $\mu$l of cosmid vector pYcl [B. Hohn et al. in "Genetic Engineering", Vol. 2, p. 169, New York 1980] linearized by EcoRI. Ligation is carried out with 300 U T4 DNA ligase (New England Biolabs) using the buffer system described by the supplier. The DNA is packaged in vitro into bacteriophase $\lambda$ [B. Hohn in "Methods in Enzymology", Vol. 68, p. 299, New York 1979] and the assembled phages are used to transduce E. coli strain HB101 ($r_k\ominus$, $m_k\ominus$, leu$\ominus$, pro$\ominus$, recA). The efficiency of transduction is about 5000 ampicillin-resistant colonies per $\mu$g of pYcl vector. 3000 amp$^R$ colonies are picked and grown individually in the wells of microtiter dishes in LB medium [10 g Bacto-Tryptone (Difco), 5 g Bacto Yeast Extract (Difco), 10 g NaCl] containing 100 $\mu$g/ml ampicillin.

b) Isolation of the yeast GAPDH gene

The gene library described above is screened with a synthetic oligonucleotide [prepared using the phosphotriester method: K. Itakura et. al., J. Am. Chem. Soc. 97, 7327 (1975); J. F. M. de Rooij et al., Recl. Trav. Chim. Pays-Bas 98. 537 (1979)] of the following structure: 5'-GCTCCATCTTCCACCGCCCC-3'. 10 $\mu$g of the oligonuclotide are kinased using 10 $\mu$l of $\gamma$-$^{32}$P-ATP (3000 Ci/mmol, 10 $\mu$Ci/$\mu$l Amersham) with T4 polynucleotide kinase (Boehringer) in a total volume of 50 $\mu$l as described by Maniatis et al. ["Molecular Cloning", Cold Spring Harbor Lab., 1982, page 125]. Colony hybridization is performed as described by the same authors (page 312). Positive clones are detected by autoradiography using Kodak X-5 X-ray film. Plasmid DNA isolation (see European Patent Application Nr. 100,561) produces a hybrid clone which contains a 2100 bp HindIII fragment coding for GAPDH [J. P. Holland et al., J. Biol. Chem. 254, 9839 (1979)]. Final proof for the authenticity of the cloned DNA comes from DNA sequencing experiment using the above mentioned oligonucleotide in combination with the dideoxy sequencing protocol as described by G. F. Hong [Bioscience Reports 1, 243 (1981)] for double stranded DNA. The cloned GAPDH gene has the same sequence as pgap491 published by Holland et al. [J. Biol. Chem. 255, 2596 (1980)].

c) Preparation of the GAPDH promoter

The 649 bp TaqI fragment which includes position -27 to -675 from the ATG of the GAPDH gene (see FIG. 6) is isolated by digesting the above mentioned hybrid plasmid with TaqI (New England Biolabs), separating the DNA fragments on a 1.2% soft agarose gel and extracting the DNA by hot phenol. Cloning of the TaqI fragment is done into the ClaI site of pBR322: 1 μg of pBR322 is cleaved with three units of ClaI (New England Biolabs) as described by the supplier. 300 ng of the phenolized and cut vector is ligated to about 300 ng of insert DNA (649 bp Taq fragment) using 200 U of T4 DNA ligase in a total volume of 20 μl. Transformation is done into *E. coli* HB101 for ampicillin resistance, plasmid DNA is prepared and analyzed by restriction analysis [TaqI, DraI]. The orientation of the TaqI fragment is established using restriction endonuclease DraI in combination with the BamHI site of the plasmids and a plasmid is selected which has the TaqI site of position -675 close to the HindIII site of pBR322. This plasmid designated pBR322/GAPDH is linearized using BamHI (New England Biolabs). The DNA is resuspended in 10 mM Tris pH 8.0 at a concentration of 0.5 μg/ml. 16 pg of SalI cleaved DNA are digested with 2 U of exonuclease Bal31 (BRL) in 100 μl of 20 mM Tris pH 8.0, 199 mM NaCl, 12 mM MgCl$_2$, 12 mM CaCl$_2$ and 1 mM EDTA. Aliquots of 2 μg DNA each are withdrawn after 1, 2, 3, 4, 5 and 6 min. of incubation at 30° C. and are immediately mixed with 50 μl phenol and 60 μl TNE. After extraction with phenol/chloroform and ethanol precipitation, the DNA is resuspended in 10 mM Tris pH 8.0 at a concentration of 100 μg/ml. To analyse the extent of exonucleolytic cleavage by Bal31 0.5 μg of DNA from each time point are digested with endonuclease BamHI and analysed on a 1.5% agarose gel in Tris-borate buffer pH 8.3 (90 mM Tris.HCl pH 8.3, 90 mM boric acid, 2.5 mM EDTA). On the average 100 bp are removed from each end of the fragment per 1 min. of Bal31 digestion.

BglII linkers (5'-GGAGATCTCC-3') are phosphorylated, annealed and ligated to the Bal31 treated DNA fragments. Excess linkers are removed by precipitation with isopropanol. The DNA is digested with BglII and directly circularized at a concentration of 5 μg/ml in a total volume of 20 μl. The size of the Bal31 shortened TaqI fragment is determined by restriction analysis (using BglII and HindIII). Three clones are selected. They contain DNA fragments that extend about 200 bp, 265 bp and 540 bp, respectively, from the ATG upstream into the GAPDH promoter. All three fragments contain the presumptive TATA box at about -140 bp. These clones still contain the origin of replication in the pBR322 derived part of the DNA and are named pGAPDH-F, pGAPDH-E and pGAPDH-D, respectively.

In order to extend the GAPDH promoter elements from the TaqI site at position -27 to a position immediately adjacent to the ATG of the GAPDH gene two synthetic complementary oligonucleotides of the following structure are synthesized:

These oligonucleotides provide the genuine GAPDH promoter sequence from position -26 to position -5 with the generation of a terminal EcoRI site. Two μg of plasmids pGAPDH-F, pGAPDH-E and pGAPDH-D are each digested with 6 units of TaqI in 50 μl and the resulting mixture is phenolized, ethanol precipitated and resuspended in 10 μl of water. The synthetic oligonucleotides are annealed by mixing 2 μl of each single strand in 100 μl of a solution containing 10 mM Tris.HCl pH 7.5, 10 mM MgCl$_2$, 50 mM NaCl, heating for 3 min. to 90° C. and slowly cooling the solution to room temperature (within about 3 hours). One μg of the TaqI digested plasmid is mixed with about a twenty fold molar excess of the annealed oligonucleotides in a volume of 20 μl and ligated for about 18 hours using 800 U of T4 DNA ligase. After inactivation of the ligase, the whole mixture is digested with 3 units of BglII (New England Biolabs). The BglII-EcoRI fragments of about 200 bp, 265 bp and 540 bp, respectively, are separated on a 1.5% soft agarose gel, extracted from the gel and ethanol precipitated.

Figure 7:
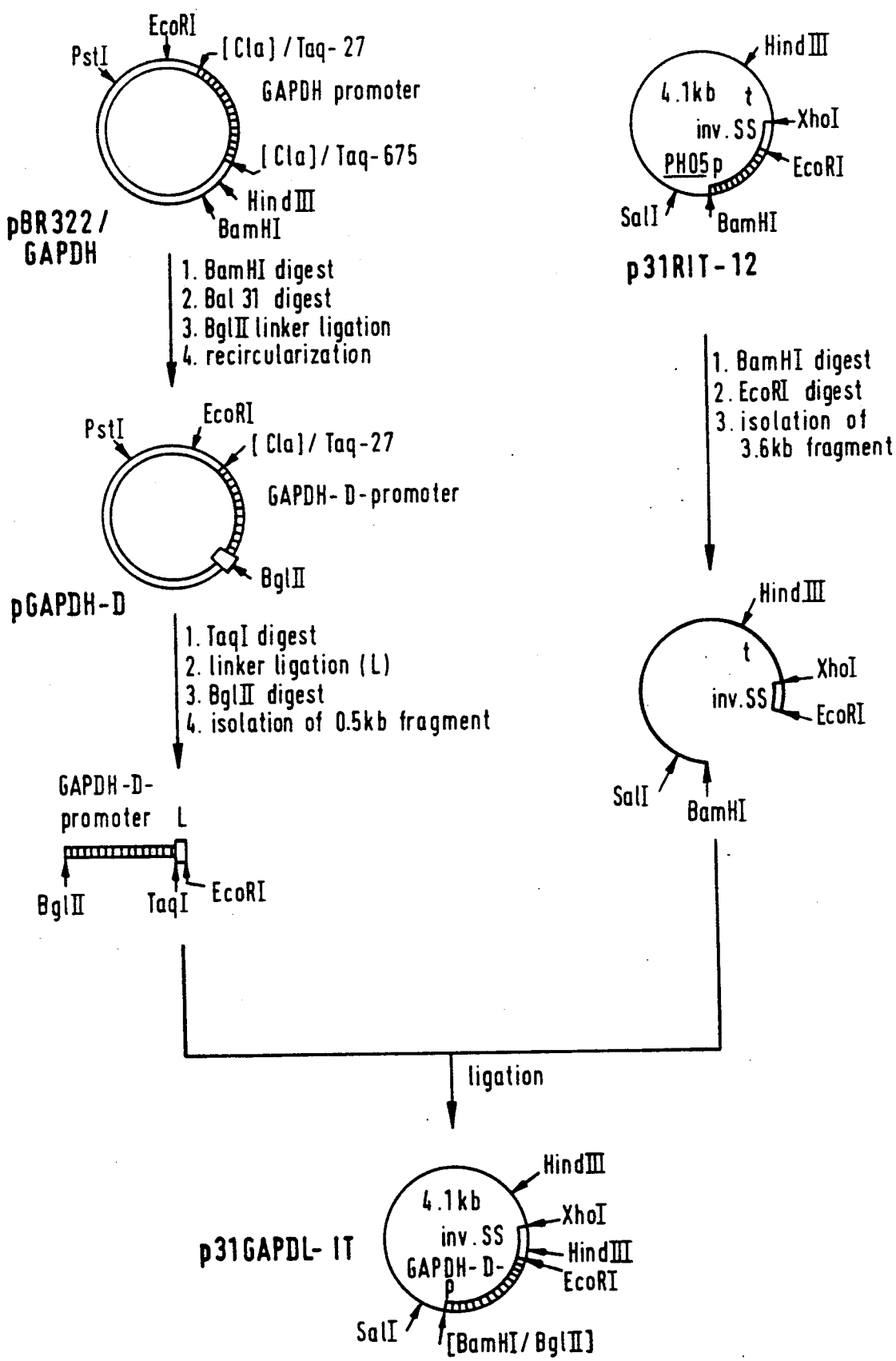
FIG. 7 depicts schematically the construction of plasmid p31GAPDL-IT.

Plasmid p31RIT-12 (see Example 2) is digested with BamHI and EcoRI. The 3.6 kb large vector fragment is isolated. This fragment is used to clone the 200 bp, 265 bp and 540 bp BglII-EcoRI GAPDH-promoter fragments. Ligation, transformation and plasmid isolation conditions are as described above. Plasmids with the correct insert are referred to as p31GAPFL-IT, p31GAPEL-IT and p31GAPDL-IT, respectively (FIG. 7).

The DNA sequences of the BglII-EcoRI fragments of plasmids p31GAPFL-IT, p31GAPEL-IT and p31GAPDL-IT are shown in FIG. 8. The exact size of these fragments is 202 bp, 267 bp and 544 bp, respectively.

Example 8

Figure 9:
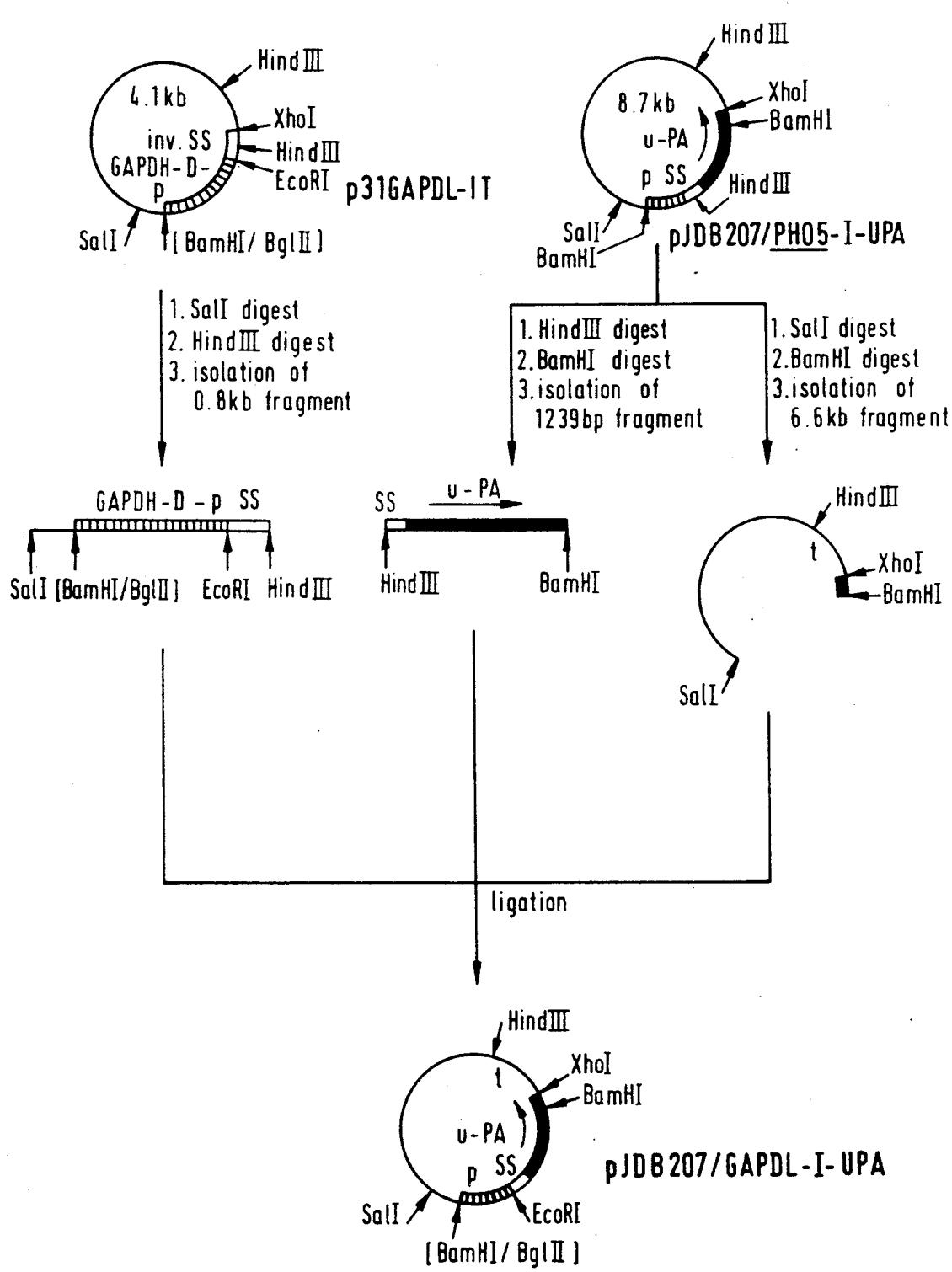
FIG. 9 shows schematically the construction of plasmid pJDB207/GAPDL-I-UPA.

Construction of plasmid pJDB207/GAPDL-I-UPA (FIG. 9)

This plasmid contains the GAPDH-D promoter, the invertase signal sequence, the coding sequence of mature urokinase and the PH05 transcription terminator in a tandem array in shuttle vector pJDB207.

Plasmid DNA of p31GAPDL-IT is digested with SalI and HindIII. A 0.8 kb SalI-HindIII fragment is separated on a preparative 1% agarose gel. This fragment contains the GAPDH-D promoter and part of the invertase signal sequence.

Plasmid pJDB207/PH05-I-UPA is digested with HindIII and BamHI. The 1239 bp HindIII-BamHI fragment comprises the remaining part of the invertase signal sequence and most of the u-PA coding sequence. pJDB207/PH05-I-UPA is also digested with SalI and BamHI. The large, 6.6 kb vector fragment is isolated on a preparative 0.6% agarose gel in tris-acetate buffer pH 8.2.

The DNA fragments are isolated by electroelution from the gel, purified by DE52 chromatography and precipitated with ethanol. The 0.8 kb SalI-HindIII fragment, the 1239 bp HindIII-BamHI fragment and the 6.6 kb SalI-BamHI vector fragment are ligated and used to transform *E. coli* HB101 Ca$^{++}$ cells. Plasmid DNA from 6 amp$^R$ transformants is analysed by HindIII and SalI restriction digests. Plasmid DNA from a single clone with the expected restriction fragments is referred to as pJDB207/GAPDL-I-UPA.

In an analogous construction a 493 bp SalI-HindIII fragment of plasmid p31GAPFL-IT (see Example 7) is isolated and used for the ligation. The resulting plasmid DNA is referred to as pJDB207/GAPFL-I-UPA.

In an analogous manner pJDB207/GAPEL-I-UPA is constructed.

Example 9

Figure 10:
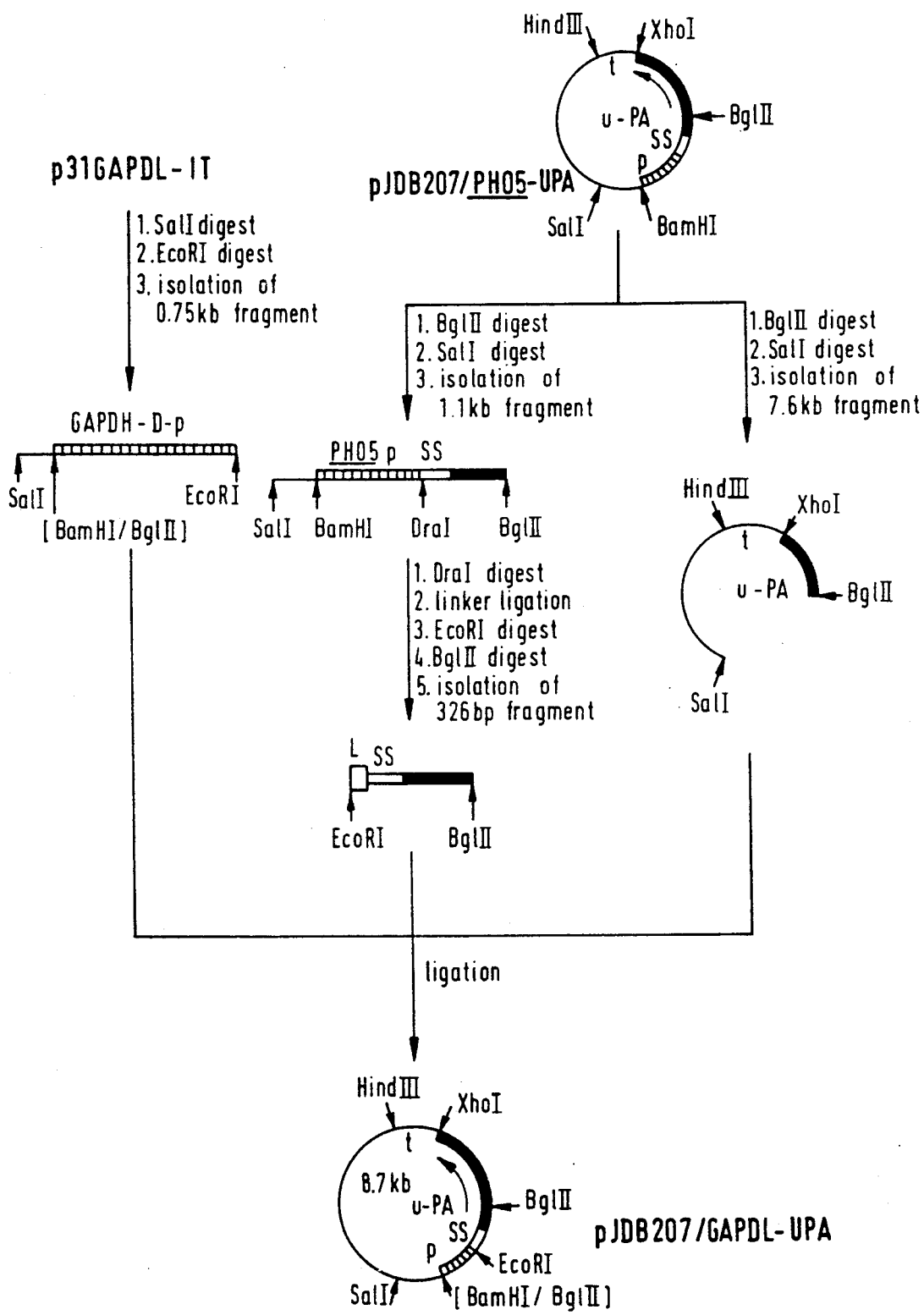
FIG. 10 is a schematic diagram depicting the construction of plasmid pJDB207/GAPDL-UPA.

Construction of plasmid pJDB207/GAPDL-UPA (FIG. 10)

A tandem array comprising the GAPDH-D promoter, the PH05 signal sequence, the urokinase coding sequence and the PH05 transcription terminator is cloned into yeast shuttle vector pJDB207.

20 μg of plasmid pJDB207/PH05-UPA are digested with BglII and SalI. The resulting two fragments are separated on a preparative 0.8% agarose gel in tris-acetate buffer pH 8.2. The 7.6 kb and 1.1 kb BglII-SalI fragments are isolated. The 1.1 kb fragment is further digested with DraI. After phenol/chloroform extraction and ethanol precipitation 3.5 pmoles of the DNA are ligated with a 100-fold excess of a kinased and annealed oligodesoxyribonucleotide linker of the formula:

with an EcoRI site and 8 nucleotides of the PH05 5' non-coding region in front of the ATG and part of the DraI recognition sequence.

After ligation for 16 h at 15° C. the ligase is inactivated, excess linkers are removed by isopropanol precipitation (0.54 volumes) in the presence of 300 mM sodium acetate pH 6.0 and 10 mM EDTA. The DNA is digested with BglII and EcoRI. A 326 bp EcoRI-BglII fragment is isolated.

Plasmid p31GAPDL-IT is digested with SalI and EcoRI. A 0.75 kb SalI-EcoRI fragment is isolated.

DNA fragments are isolated by electroelution from the agarose gel, purified by DE52 chromatography and precipitated with ethanol. 0.2 pmoles of the 0.75 kb SalI-EcoRI fragment, 0.4 pmoles of the 326 bp EcoRI-BglII fragment and 0.1 pmoles of the 7.6 kb SalI-BglII vector fragment ar ligated for 5.5 h at 15° C. 1 μl of the ligation mixture is used to transform E. coli HB101 Ca++ cells. 10 amp$^R$ transformants are grown and plasmid DNA is prepared. The Plasmid DNA is analysed by EcoRI restriction digests. Plasmid DNA from a single clone with the expected restriction pattern is referred to as pJDB207/GAPDL-UPA.

In an analogous manner, plasmids pJDB207/GAPFL-UPA and pJDB207/GAPEL-UPA are constructed.

Example 10

Figure 11:
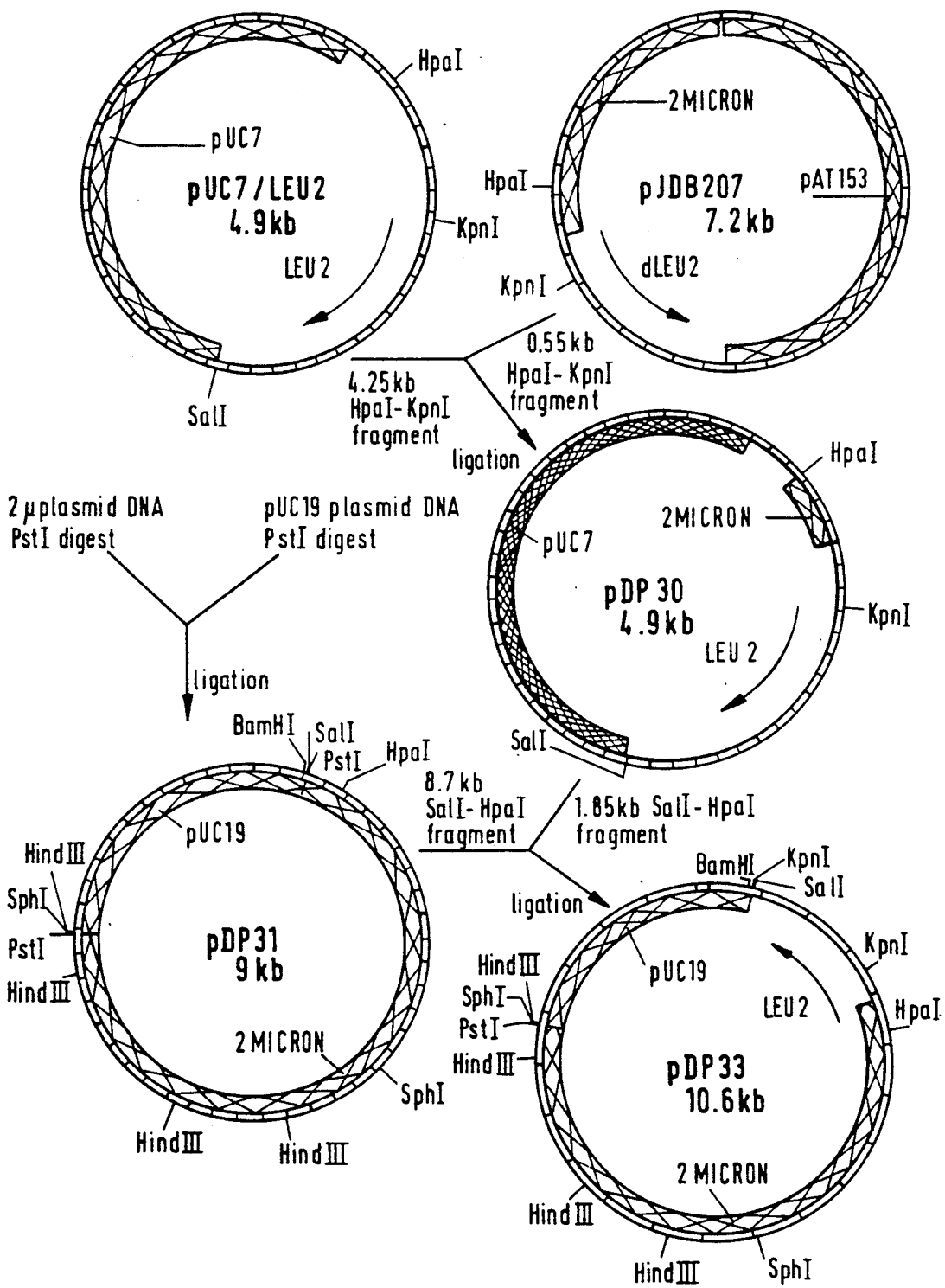
FIG. 11 and FIG. 12 show schematically the construction of plasmid pDP38 via plasmid pDP33.
Figure 12:
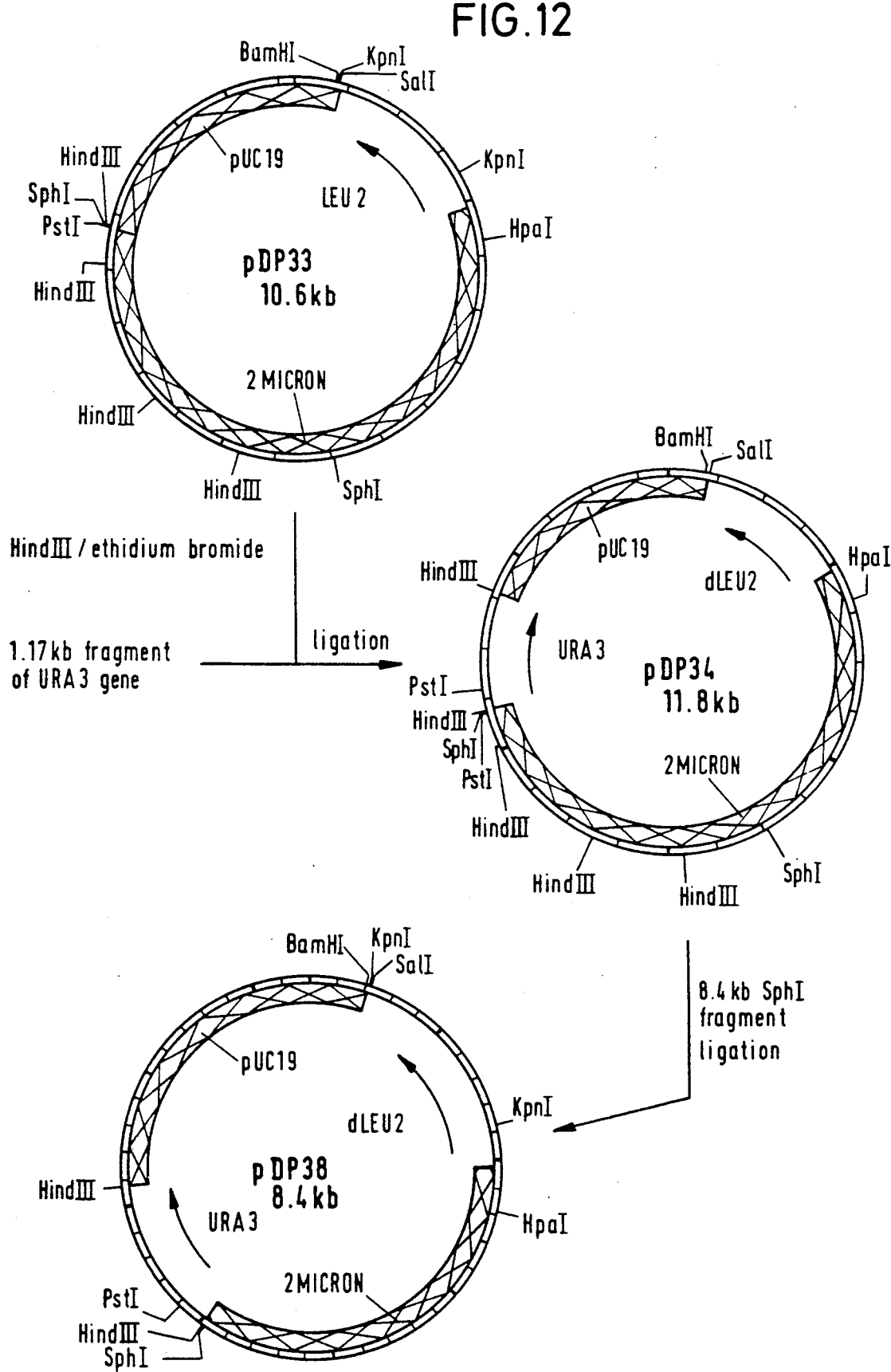

Construction of plasmid pDP38 (FIG. 11 and FIG. 12)

2 micron covalently closed circle DNA is isolated from Saccharomyces cerevisiae strain S288C by digesting the cell wall with 5 μg/ml Zymolyase 100,000 units/μg for 20 min at 37° C., then lysing the cells with 2% SDS. EDTA is then added to 25 mM, caesium chloride to a final density of 1.55 g/ml, ethidium bromide to 1 mg/ml, and then the whole transferred to an ultracentrifuge tube. Plasmid DNA is separated from the chromosomal DNA by ultra-centrifugation for 42 hours at 42,000 rpm at 15° C. The 2 micron plasmid DNA is cut from the gradient with a syringe. The ethidium bromide is removed with NaCl saturated isopropanol and the plasmid DNA is finally ethanol precipitated. The purified plasmid DNA is then linearised with PstI and cloned into the PstI site of pUC19 [J. Norrander et al., Gene 26, 101 (1983)] to give plasmid pDP31. Plasmid pJDB207 is digested with the enzymes KpnI and HpaI. The resulting 0.55 kb fragment is purified and cloned into the 4.25 kb KpnI-HpaI fragment of plasmid pUC7-/LEU2 [a plasmid containing the yeast genomic 2.2 kb XhoI-SalI LEU2 gene [A. Andreadis et al. Cell 31, 319 (1982)] cloned into the SalI site of the plasmid pUC7 [J. Vieira et al. Gene 19, 259 (1982)]]. This results in plasmid pDP30 where the original 2 micron/LEU2 fusion as in plasmid pJDB207 is placed in front of the LEU2 gene plus its complete terminator. pDP30 is digested with HpaI and SalI and the 1.85 kb fragment containing the complete LEU2 gene is purified and cloned into the 8.7 kb HpaI-SalI fragment of plasmid pDP31. The resulting plasmid, pDP33, is linearised with HindIII in the presence of 50 μg/ml ethidium bromide [M. Oesterlund et al. Gene 20, 121 (1982)] and ligated with the 1.17 kb HindIII fragment containing the URA3 gene [M. Rose et al. Gene 29, 113 (1984)]. Positive insertion of the URA3 gene is selected for by transformation into the E. coli strain pyrf [M. Rose et al., supra]. This gives plasmid pDP34. pDP34 is digested with the enzyme SphI. The resulting 8.4 kb fragment is purified and self ligated to give plasmid pDP38.

Example 11

Construction of plasmids pDP38/GAPDL-I-UPA and pDP38/GAPDL-UPA

Vector pDP38 (see Example 10) contains the LEU2 and URA3 genes, pBR322 sequences and part of the yeast 2 micron DNA. Plasmid pDP38 is linearized with BamHI. The resulting sticky ends are filled in a reaction with Klenow DNA polymerase (Maniatis et al., p. 113, supra). The DNA is further digested to completion with SalI and the large 8.4 kb fragment is isolated.

10 μg of plasmid pJDB207/GAPDL-I-UPA are partially digested with HindIII (1 unit/pg DNA) in the presence of 10 μg/ml of ethidium bromide for 28 min at 37° C. The reaction is stopped by the addition of EDTA to a final concentration of 10 mM. The sticky ends of the DNA are filled in a reaction with Klenow DNA polymerase. The DNA is further digested with SalI. A 2.2 kb SalI-[HindIII]/blunt end fragment is isolated.

The purified DNA fragments are ligated and transformed into E. coli HB101 Ca++ cells. 24 amp$^R$ colonies are grown up. Plasmid DNA is prepared and analysed by EcoRI and SalI/HindIII restriction digests. Plasmid DNA of a single clone with the expected restriction fragments is referred to as pDP38/GAPDL-I-UPA.

In an analogous construction a 2.2 kb SalI-[HindIII]/blunt end fragment is isolated from pJDB207/GAPDL-UPA after complete HindIII digestion, Klenow DNA polymerase reaction and SalI digestion. This fragment is ligated into pDP38 as described above. A single clone is referred to as pDP38/GAPDL-UPA.

In an analogous way the 2.2 kb SalI-[HindIII]/blunt end fragments are isolated from pJDB207/GAPEL-I-UPA, pJDB207/GAPFL-I-UPA, pJDB207/GAPEL-UPA and pJDB207/GAPFL-UPA. The purified fragments are ligated into pDP38. The ligation mixture is used to transform E. coli HB101.

Plasmid DNA of a single clone each is referred to as pDP38/GAPEL-I-UPA, pDP38/GAPFL-I-UPA, pDP38/GAPEL-UPA and pDP38/GAPFL-UPA.

Example 12

Transformation of S. cerevisiae strains HT246 and GRF18

*Saccharomyces cerevisiae* strain HT246 (a, leu2-3, leu2-112, prb) is transformed with plasmids
pJDB207/PH05-UPA
pJDB207/PH05-I-UPA
pJDB207/PH05-SSUPA
pJDB207R/PH05-UPA
pJDB207/GAPDL-UPA
pJDB207/GAPFL-UPA
pJDB207/GAPDL-I-UPA
using the transformation protocol described by Hinnen et al. [Proc. Natl. Acad. Sci. USA 75, 1929 (1978)]. Transformed yeast cells are selected on yeast minimal media plates deficient in leucine. Single transformed yeast colonies are isolated and referred to as

*Saccharomyces cerevisiae* HT246/pJDB207/PH05-UPA
*Saccharomyces cerevisiae* HT246/pJDB207/PH05-I-UPA
*Saccharomyces cerevisiae* HT246/pJDB207/PH05-SSUPA
*Saccharomyces cerevisiae* HT246/pJDB207R/PH05-UPA
*Saccharomyces cerevisiae* HT246/pJDB207/GAPDL-UPA
*Saccharomyces cerevisiae* HT246/pJDB207/GAPFL-UPA
*Saccharomyces cerevisiae* HT246/pJDB207/GAPDL-I-UPA In an analogous manner, *Saccharomyces cerevisiae* strain GRF18 (DSM 3665) is transformed with the above mentioned plasmids. The resulting transformed yeast strains are designated

*Saccharomyces cerevisiae* GRF18/pJDB207/PH05-UPA
*Saccharomyces cerevisiae* GRF18/pJDB207/PH05-I-UPA
*Saccharomyces cerevisiae* GRF18/pJDB207/PH05-SSUPA
*Saccharomyces cerevisiae* GRF18/pJDB207R/PH05-UPA
*Saccharomyces cerevisiae* GRF18/pJDB207/GAPDL-UPA
*Saccharomyces cerevisiae* GRF18/pJDB207/GAPFL-UPA
*Saccharomyces cerevisiae* GRF18/pJDB207/GAPDL-I-UPA.

Example 13

Transformation of Saccharomyces cerevisiae strain HT350

*S. cerevisiae* strain HT350 is obtained by crossing strain *S. cerevisiae* HT246 with a ura-3 deficient strain such as *S. cerevisiae* HT285 (α, his3-11, his3-15, leu2-3, leu2-112, ura3, pep4-3) which results in the following genotype for strain HT350 (α, his3-11, his3-15, leu2-3, leu2-112, ura3, prb. pep4-3). Strain HT350 is transformed with the plasmids pDP38/GAPDL-I-UPA, pDP38/GAPFL-I-UPA, pDP38/GAPEL-I-UPA, pDP38/GAPDL-UPA, pDP38/GAPFL-UPA, and pDP38/GAPEL-UPA, respectively, using the transformation protocol by Hinnen et al. (supra). Transformed yeast cells are selected on yeast minimal media plates deficient in uracil and supplemented with leucine. Single transformed yeast colonies are isolated and referred to as

*Saccharomyces cerevisiae* HT350/pDP38/GAPDL-I-UPA
*Saccharomyces cerevisiae* HT350/pDP38/GAPFL-I-UPA
*Saccharomyces cerevisiae* HT350/pDP38/GAPEL-I-UPA
*Saccharomyces cerevisiae* HT350/pDP38/GAPDL-UPA
*Saccharomyces cerevisiae* HT350/pDP38/GAPFL-UPA
*Saccharomyces cerevisiae* HT350/pDP38/GAPEL-UPA

Example 14

Fermentation of transformed yeast strains

*Saccharomyces cerevisiae* HT246/pJDB207/PH05-UPA,
*Saccharomyces cerevisiae* HT246/pJDB207/PH05-I-UPA and
*Saccharomyces cerevisiae* HT246/pJDB207R/PH05-I-UPA contain plasmids with the full length PH05 promoter and require derepression of the promoter for expression of scu-PA. Cells of the *S. cerevisiae* HT246 transformants are each grown in 10 ml of yeast minimal medium (Difco Yeast Nitrogen Base without amino acids to which 2% glucose and 20 mg/l L-histidine are added) in a 50 ml Erlenmeyer flask with shaking at 30° C. for 24 h until a density of $5-7 \times 10^7$ cells/ml is reached. The cells of the preculture are then washed in 0.9% NaCl and 20% of the preculture cells are used to inoculate 50 ml of a low $P_i$ minimal medium prepared according to the recipe of the Difco Yeast Nitrogen Base medium (without amino acids), but containing 0.03 g/l $KH_2PO_4$, 10 g/l L-aspargine instead of $(NH_4)_2SO_4$, 20 g/l glucose and 1 g/l L-histidine. The cultures are agitated at 30° C. for up to 48 h at 180 revs/min. Final densities of $1 \times 10^8$ cells/ml ($\hat{=} OD_{600} = 4-5$) are obtained.

Yeast transformants comprising plasmids with GAPDH promoter of different length express scu-PA constitutively.

Corresponding transformants containing pJDB207 derived plasmids are grown in the yeast minimal medium preculture (supra). 20% of the washed preculture is inoculated into 50 ml of the complex main culture medium consisting of (g/l): peptone 5, yeast extract 10, glucose 20, sucrose 40, $(NH_4)_2SO_4$ 3, $KH_2PO_4$ 2, $MgSO_4$ 0.5, NaCl 0.1, $CaCl_2$ 0.1, biotin 10 µg/l. Approximately $1 \times 10^9$ cells/ml ($\hat{=} OD_{600}$ 40-45) are obtained after 48 h of incubation at 30° C. and 200 revs/min.

Corresponding transformants comprising pDP38 derived plasmids are cultivated under uracil selection. The cells are grown for 24 h at 30° C. and 180 revs/min in a preculture medium consisting of (g/l): casamino acids 4.5, yeast extract 6.5, sucrose 20, glucose 20, $(NH_4)_2SO_4$ 3.6, $KH_2PO_4$ 1, $MgSO_4$ 0.2, $CaCl_2$ 0.013, trace elements.

10% of the washed preculture cells are used to inoculate 50 ml selective main culture medium consisting of (g/l): Yeast Nitrogen base (Difco, without amino acids) 5, L-asparagine 7.5, casamino acids 8.5, methyl-ethylsulfonat 10, adenine 0.05, L-histidine 0.04, L-leucine 0.1, L-tryptophan 1, Ca-pantothenate 0.03, glucose 30.

Approximately $8 \times 10^8$ cells/ml ($\triangleq OD_{600}$ ca. 35) are obtained after 48 h of incubation at 30° C. and 200 revs/min.

Cells from 2 ml are collected after 24 h and 48 h, respectively, by centrifugation at 3000 rpm for 10 min in Falcon 2070 tubes. The cells are washed once with 0.9% NaCl and centrifuged. The cell pellet is suspended in lysis buffer [66 mM potassium phosphate pH 7.4, 4 mM Zwittergent (Calbiochem)]. To the cell suspension are added 8 g of glass beads (0.5–0.75 mm in diameter) and the suspension is shaken on a Vortex Mixer [Scientific Instruments Inc. USA) at full speed for $4-5 \times 2$ min. More than 90% of the cells are broken by this procedure. Cell debris and glass beads are sedimented by centrifugation for 5 min at 3000 rpm at 4° C. Immediately before testing the biological activity the supernatants are diluted up to 500 fold in 0.1 M Tris-HCl pH 7.4, 0.05% Tween 80, 0.1% bovine serum albumin.

Example 15

Determination of biological activity

Amidolytic activity of scu-PA may be measured directly using the Kabi (KabiVitrum, Stockholm, Sweden) synthetic tripeptide chromogenic substrate S-2444 (pyro-Glu-Gly-Arg-pNA). For the determination of the content of tcu-PA cleaved at Lys158 and/or Lys136 the assay is carried out according to the manufacturer's recommendations (without plasmin activation). Scu-PA requires plasmin activation prior to the determination of its amidolytic activity leading to the following modification of the direct assay: 100 μl scu-PA containing samples (see Example 14) are preincubated with 0.01 U human plasmin (Boebringer Mannheim, Germany) for 60 min at 37° C. 5 I.U. aprotinin (Boehringer Mannheim, Germany) are added and the mixture incubated for a further 10 min at 100 m temperature before the chromogenic substrate S-2444 (supra) is added.

Quantitation of the activity is done by comparison with the WHO urokinase standard (lot 66/46) and expressed in International Units (I.U.). According to the commercial preparation Ukidan ® (Serono, Freiburg, Germany), highly purified urokinase isolated from human urine has a specific activity of 70,000–100,000 I.U./mg protein.

Scu-PA content may also be measured via its plasminogen activation using the synthetic tripeptide substrate S-2251 (KabiVitrum, Stockholm, Sweden). The assay is done according to the manufacturer's recommendation (KabiVitrum, supra) with scu-PA containing samples as plasminogen activator instead of streptokinase.

The amount of antigen present in yeast fermentation broths is estimated using the dot blotting procedure (Bio-Rad, Richmond, USA). A polyclonal rabbit anti-human urine urokinase antibody is used for detection.

Samples are taken at 24 h of fermentation and are pre-treated as described in Example 14. A summary of the plasminogen activating (S-2251 as substrate) activities with different plasmids in 2 different strains is given in Table 1.

TABLE 1

| plasmid | host | selection | S-2251 activity I.U./2 × $10^7$ cells |
|---|---|---|---|
| pJDB207R/PH05-UPA | HT246 | leu | 0 |
| pJDB207/PH05-SSUPA | HT246 | leu | 2.2 |
| pJDB207/PH05-I-UPA | HT246 | leu | 10 |
| pJDB207/PH05-UPA | HT246 | leu | 1.4 |

TABLE 1-continued

| plasmid | host | selection | S-2251 activity I.U./2 × $10^7$ cells |
|---|---|---|---|
| pJDB207/GAPDL-UPA | HT246 | leu | 9 |
| pDP38/GAPDL-I-UPA | HT350 | leu | .3 |
| pDP38/GAPDL-I-UPA | HT350 | ura | 5.7 |
| pDP38/GAPFL-I-UPA | HT350 | leu | 0.4 |
| pDP38/GAPFL-I-UPA | HT350 | ura | 3.4 |

A comparison of the activities determined in the 3 assays used is given in Table 2.

Indicated are total volumetric titers (per ml culture broth) obtained after 48 h fermentation of strain HT246 using the plasmid pJDB207/GAPDL-I-UPA.

TABLE 2

| I.U./ml culture broth | | | |
|---|---|---|---|
| Activity on | | | |
| S-2444 without plasmin | S-2444 with plasmin | Activity on S-2251 | Dot-blotting (estimation) |
| 25.8 | 215 | 1670 | ca. 1000 |

The results indicate that best scu-PA production in yeast is obtained when the DNA construction includes a yeast signal sequence such as the PH05 or invertase signal sequence. The results further indicate that scu-PA is expressed in different yeast host-backgrounds, whereby fermentation under selective conditions (either low Pi minimal medium or uracil selection) leads to relatively higher specific productivity per OD.

About 90% of the expression product is scu-PA as indicated in the activity measurements on S-2444 with or without plasmin activation. Dot-blotting indicates that the amount of antigen present is not exceeding significantly the amount of biological activity measured. Therefore yeast recombinant scu-PA is correctly folded as in genuine scu-PA.

Example 16

Recovery of scu-PA from yeast cells (30 l culture broth)

S. cerevisiae strain HT246/pJDB207/GAPDL-I-UPA is grown in the same way as S. cerevisiae strain GRF18/pJDB207/GAPFL-HIR in the production of hirudin (cf. European Patent Application No. 225633). The content of scu-PA inside the cells (after disintegration, see Example 14) is determined by the indirect amidolytic assay using the substrate S-2251 (see Example 15). After 48 h of incubation the cells are harvested by centrifugation in a Sharples centrifuge (Appareils Centrifuges, Rueil, France) and suspended in an equal volume of lysis buffer [200 mM $K_2HPO_4$, 0.2% Tween 80]. The cells are then broken in a glass bead mill (Dyno-Mill, KDL, Bachofen AG, Basel; 4500 rpm, 18 l/h). The suspension is diluted 5 times with 150 mM NaCl, 0.05% Tween 80, and the cell debris are sedimented in the presence of 0.6 0/00 polyethyleneimine at 4° C. by centrifugation in a Westfalia separator SB7-47. The slightly turbid supernatant is filtered through a Zetapor Cartridge (0.22 μm pore width) and adjusted to pH 6.05 with 1N HCl. 1 l of cation exchanger S-Sepharose fast flow (Pharmacia) per kg of sedimented yeast cells is added and the suspension is stirred for 1 h at 4° C. The beads are then transferred to a column of diameter 9 cm and washed with 50 mM sodium phosphate pH 7.0, 150 mM NaCl, 0.05% Synperonic. Scu-PA is eluted at a flow rate of 30 ml/min with the same buffer containing 250 mM NaCl. To the fractions containing the scu-PA [as measured in the direct amidolytic assays; cf. Example 15] concanavalin A Sepharose (Pharmacia) is added (1 ml gel per 0.2 mg scu-PA) and the suspension stirred for 45 min at 4° C. After washing with 1M NaCl 10 mM sodium phosphate pH 7.0, 0.05% Synperonic, the beads are transferred to a column of diameter 4.4 cm and scu-PA is eluted with 0.8 M methyl-α-D-mannopyranoside, 150 mM NaCl, 20 mM sodium acetate pH 4.0, 0.05% Synperonic at a flow rate of 1 l/h. To the fractions containing scu-PA, antiurokinase IgG-Sepharose is added [purified polyclonal rabbit antibody (IgG-fraction) raised against human urinary urokinase] and the suspension is stirred for 45 min at 4° C. The beads are then transferred to a column of diameter 2.2 cm and washed with 1M NaCl, 10 mM sodium phosphate pH 7.0, 0.05% Synperonic. Scu-PA is eluted with 0.1M glycine-HCl pH 2.4, 0.05% Synperonic at a flow rate of 1 ml/min. The fractions containing scu-PA are adjusted to pH 6 with 1N NaOH.

At this stage about 25–30% of the total activity consists of tcu-PA as identified by the direct amidolytic assay (cf. Example 15).

The effluent from the antibody column is applied to a Mono-S column (1 ml bed volume; Pharmacia) equilibrated with 50 mM sodium phosphate ph 6.0, 0.05% Synperonic. After washing with the equilibration buffer, scu-PA is eluted with a step-like gradient of the equilibration buffer and a buffer B composed of 500 mM NaCl, 50 mM sodium phosphate pH 7.0, 0.05% Synperonic at a flow rate of 1 ml/min. By this elution, two activity peaks are observed, one peak eluted at the first step at 30% of buffer B and the other at the second step at 55% of buffer B. The direct amidolytic assay revealed that the fraction eluted at 30% B exhibits still a high amount of tcu-PA, whereas the fraction eluted at 55% B exhibits as little as 1–3% tcu-PA.

Yeast scu-PA produced in this manner migrates as a single band of about 51 KD molecular weight in SDS polyacrylamide gel electrophoresis under non-reducing conditions. The scu-PA obtained has a purity of about or more than 95% as judged by the direct amidolytic assay (cf. Example 15) and by SDS-polyacrylamide gel electrophoresis under reducing conditions.

Example 17

Glycosylation state of yeast scu-PA

Glycosylation is determined with a $^{125}$I-concanavalin A overlay assay after gel electrophoresis. Concanavalin A is a plant lectin which specifically recognizes mannose residues. Purified scu-PA from yeast as well as u-PA standard Ukidan ® (Serono, Freiburg, Germany) are subjected to gel electrophoresis on 10% gels. Proteins are then fixed to the gel in 7% acetic acid for 30 min. The gel is washed in lectin buffer having the following composition:
0.15 M NaCl
50 mM Tris-HCl pH 7.4
0.5 mM $CaCl_2$
0.5 mM $MnCl_2$
Washing is continued until the pH reaches about 7.3.

The gel is then carefully overlayered with 2 ml lectin buffer containing 3 mg hemoglobin, 100 μg concanavalin A and 2 μCi $^{125}$I-concanavalin A.

Another otherwise identical gel is overlayered with the mix mentioned above supplemented with 0.2 M α-methyl-mannoside. After 3 h incubation in a humidified chamber the gels are extensively washed in lectin buffer, dried and exposed to X-ray films. Without α-methyl-mannoside both Ukidan ® and yeast scu-PA are stained with $^{125}$I-concanavalin. Their molecular weights are essentially identical. In the presence of α-methyl-mannoside, a competitive inhibitor of lectin-binding, the human urinary urokinase disappears, whereas yeast scu-PA is still visible. This indicates that yeast scu-PA is glycosylated and that its glycosylation is of a different type compared to human urinary urokinase.

Example 18

Further purification of scu-PA

A solution of scu-PA (cf. Example 16) dialyzed against 0.05 M Tris-HCl pH 8.0, 0.05% Tween 80, 0.05 M NaCl is loaded onto 3 ml of a benzamidine-Sepharose column (Pharmacia, Uppsala, Sweden) and washed with the Tris-HCl pH 8.0 buffer containing 1 M NaCl. Scu-PA is fully recovered in the flow-through and in the wash-solution whereas the byproduct tcu-PA can be eluted from the column with 0.05 M Tris-HCl pH 8.0 buffer, containing 1 M L-arginine. The scu-PA obtained has a purity of about or more than 98%.

Example 19

Mutation of the glycosylation site at [Asn302] of the urokinase B-chain a) Cloning of a PstI-BamHI fragment of u-PA into M13mp18: The plasmid pJDB207/PH05-1-UPA (see Example 3) contains the complete coding region of urokinase. The DNA is cut with PstI and BamHI. The 886 bp PstI-BamHI fragment from the urokinase gene contains the glycosylation site (Asn302) at nucleotide positions 1033–1041. Another fragment of similar size is further cut by BstEII. The 886 bp PstI-BamHI fragment is isolated on a preparative 0.8% agarose gel.

M13mp18 RF-DNA is cut with PstI and BamHI. The 7.3 kb fragment is isolated on a preparative 0.8% agarose gel. The DNA fragments are electroeluted from the agarose gel and purified by DE52 chromatography and ethanol precipitation.

0.1 pmoles of the 7.3 kb PstI-BamHI cut vector and 0.2 pmoles of the 886 bp PstI-BamHI u-PA fragment are ligated. 1 μl and 3 μl of the ligation mixture are used for transformation of E. coli JM109 $Ca^{2+}$ cells according to the manual "M13 cloning and sequencing handbook" published by Amersham. 12 colourless plaques are picked and single-strand DNA is prepared [J. Messing, Methods in Enzymology 101, 21–78 (1983)]. The single-stranded DNA is used to prepare partially double-stranded DNA by annealing and extending the M13 universal primer with Klenow polymerase. The reaction product is extracted with phenol/chloroform and the DNA is precipitated with ethanol. The DNA is cut with PstI and BamHI. A 886 bp fragment indicates that the u-PA fragment has been cloned in the M13mp18 vector. One clone is further analysed and the correct insert is confirmed by sequencing. The clone is referred to as M13mp18/UPA.

b) Mutation of the glycosylation site at Asn302:

```
                                    302
                                   [Asn] Ser  Thr
M13mp18 insert:  3'... AAA CCT TTT CTC TTA AGA TGG CTG ATA ... 5'
(antisense strand)

mutagenic
primer W:        5'-GGA AAA GAG CAA TCT ACC GAC-3' mutated
sense strand:    5'... TTT GGA AAA GAG CAA TCT ACC GAC TAT ... 3'
                        •                          •
                       1024         [Gln]         1044 sequencing primer: CTGCCCTCGATGTATAACG
                   •                 •
                  967               985
```

The mutagenic and sequencing primers are synthesized using the phosphoramidite method [M. H. Caruthers, in: Chemical and Enzymatic Synthesis of Gene Fragments, (ed. H. G. Gassen and A. Lang) Verlag Chemie, Weinheim, Federal Republic of Germany] on an Applied Biosystem Model 380B synthesizer.

In vitro mutagenesis on single-stranded template DNA is performed as described by T. A. Kunkel [Proc. Nat. Acad. Sci. USA 82, 488–492 (1985)]. Uracil containing single-stranded template DNA is produced by one cycle of growth on the E. coli strain RZ1032 (dut⁻, ung⁻).

100 pmoles of the mutagenic oligonucleotide primer W are phosphorylated in 20 μl of 50 mM Tris-HCl pH 7.5, 10 mM MgCl₂, 5 mM DTT, 0.5 mM ATP and 20 units of T4 polynucleotide kinase (Boehringer). After 30 min at 37° C. the reaction is stopped by heating to 70° C. for 10 min.

0.3 pmoles of uracil containing M13mp18/UPA template DNA is incubated with 10 pmoles of phosphorylated mutagenic oligodesoxyribonucleotide primer W and 10 pmoles of M13 universal sequencing primer in 30 μl of 10 mM Tris-HCl pH 8.0, 10 mM MgCl₂. The sample is heated to 80° C. and allowed to cool to room temperature in a small water-bath.

c) Extension-ligation reaction:

To the above annealed sample 10 μl of an enzyme-dNTP mixture is added containing 1 mM dNTPs, 10 mM Tris-HCl pH 8.0, 10 mM MgCl₂, 20 mM DTT, 1 mM ATP, 400 units of T4 DNA ligase (Biolabs, 400 U/μl) and 6 units of Klenow DNA polymerase (Boehringer, 6 U/μl). Incubation is at 15° C. overnight.

d) Transformation of E. coli BMH71 cells:

The ligation mixture is diluted to 200 μl with TE. 0.1 μl, 1 μl and 10 μl of the extension-ligation mixture are added to competent E. coli BMH71 Ca²⁺ cells (Kunkel, supra). After 30 min on ice the cells are heat-shocked for 3 min at 42° C. and then kept on ice. Cells are plated with top agar and E. coli JM101 indicator cells.

6 plaques are picked and used to infect E. coli JM109. Phages are isolated from the supernatant by PEG precipitation. Single-stranded DNA is prepared by extraction with phenol and precipitation with ethanol. Template DNAs are resuspended in TE.

Mutation of the AAT codon (Asn302) to the CAA codon (Gln302) is confirmed for one clone by DNA sequence determination with the above mentioned sequencing primer using the chain termination method [F. Sanger et al., Proc. Nat. Acad. Sci. USA 74, 5463–67 (1977)]. The mutation results in an Asn→Gln change in amino acid position 302 of u-PA and thereby eliminates the single glycosylation site in urokinase. W designates the mutation of the glycosylation site in the u-PA B-chain (Asn302→Gln302). No other mutations are found in the u-PA coding sequence. The positive clone is referred to as M13mp18/UPA-W.

Example 20

Mutation of [Lys135]→Gly:

The proteolytic cleavage of scu-PA at the Lys135-Lys136 bond leads to the formation of low molecular weight urokinase. The dibasic cleavage site is eliminated by in vitro mutation of [Lys135] to glycine.

```
                                  135  136
                                 [Lys] Lys
M13mp18 insert:  3'... ACG CGT CTA CCT TTT GGG AGG AGA ... 5'
(antisense strand)

mutagenic primer LG    5'-GCA GAT GGA GGT AAG CCC TCC -3' mutated sense    5'... TGC GCA GAT GGA GGT AAG CCC TCC TCT ... 3'
strand                 •                 •                 •
                      534               [Gly]             543
```

The procedure for in vitro mutagenesis is described in Example 19. Mutated single stranded sense strand is prepared. The mutation of the AAA codon (Lys135) to the GGT codon (Gly) is confirmed by DNA sequencing using the M13 univeral primer (Biolabs). The mutation [Lys135]→Gly results in the elimination of the proteolytic cleavage site at amino acid 135 in the A chain of urokinase. One clone with the mutated DNA is referred to as M13mp18/UPA-LG.

Example 21

Mutation of [Lys135]→Ser:

Amino acid [Lys135] is mutated to serine in a way analogous to Example 20.

```
                               135  136
                              [Lys]Lys
M13mp18 insert:    3'... ACG CGT CTA CCT TTT TTC GGG AGG AGA ... 5'
(antisense strand)

mutagenic primer LG    5'-GCA GAT GGA AGT AAG CCC TCC -3' mutated sense     5'... TGC GCA GAT GGA AGT AAG CCC TCC TCT ... 3'
strand                •              [Ser]              •
                     523                                543
```

The mutation of the AAA codon (Lys135) to the AGT codon (Ser) is confirmed by sequencing single stranded template DNA using the M13 universal primer. One clone with the correct mutation is referred to as M13mp18/UPA-LS.

Example 22

Mutation of [Phe157]→Asp:

Single chain u-PA is converted to two chain u-PA by proteolytic cleavage by plasmin of the Lys158-Ile159 bond. Thrombin cleaves the Arg156-Phe157 bond. To prevent proteolytic cleavage of scu-PA by plasmin and thrombin [Phe157] is mutated to Asp.

5 μg of DNA are digested with BamHI and PstI. After adding 2 μg of RNase (Serva) and incubating 5 min at 37° C. the 886 bp PstI-BamHI fragment is isolated on a preparative 0.8% agarose gel. The DNA fragment is electroeluted and precipitated in ethanol. The fragment contains the mutation AAT→CAA at nucleotide positions 1033-1035 (Asn302→Gln) in the urokinase B-chain. 0.2 pmoles each of the 1.2 kb SalI-PstI fragment and the 886 bp PstI-BamHI fragment and 0.1 pmoles of the 6.6 kb SalI-BamHI vector fragment are ligated. Competent E. coli HB101 $Ca^{2+}$ cells are transformed.

12 ampicillin resistant transformants are grown. Plasmid DNA is isolated and analyzed by EcoRI and Hin-

```
                        156  157  158  159
                        Arg [Phe] Lys  Ile
M13mp18 insert    3'... GA GAC TCC GGG GCG AAA TTC TAA TAA CCC CC ... 5'
(antisense strand)

mutagenic primer P   5'- G AGG CCC CGC GAC AGG ATT ATT G -3' mutated sense    5'... CT CTG AGG CCC CGC GAC AAG ATT ATT GGG GG ... 3'
strand               •              [Asp]              •
                    588                                610
```

The mutation of the TTT codon (Phe157) to the GAC codon (Asp157) is confirmed by DNA sequencing using the M13 universal primer (Biolabs). The mutation [Phe157]→Asp results in the elimination of the proteolytic cleavage sites for thrombin at amino acid position 156 and plasmin at amino acid position 158 in the single chain urokinase. One clone with the mutated DNA is referred to as M13mp18/UPA-P.

Example 23

Transfer of the mutation [Gln302] from the M13 clone to the yeast expression cassette M13mp18/UPA-W contains a mutated DNA insert coding for an amino acid sequence with a single change (Gln302) which eliminates the glycosylation site in the urokinase B-chain. The DNA fragment with the mutation is transferred to the yeast expression plasmid pJDB207/PH05-I-UPA.

Plasmid pJDB207/PH05-I-UPA is cut with SalI and BamHI. The 6.6 kb vector fragment is isolated. It contains the 3' part of the u-PA gene from the BamHI site at nucleotide position 1323 (FIG. 1) to the position 1441 (PvuII site with XhoI linkers added) and the PH05 transcription termination signals.

pJDB207/PH05-I-UPA is digested with SalI and PstI. The 1.2 kb SalI-PstI fragment is isolated and electroeluted from the gel. The DNA fragment contains the SalI-BamHI sequence of pBR322, the PH05 promoter, the invertase signal sequence and the u-PA coding sequence up to the PstI site.

RF-DNA is prepared for M13mp18/UPA-W (see Example 19) by the quick DNA isolation procedure [D. S. Holmes et al., Analyt.Biochem. 114 (1981), 193-197].

dIII restriction cuts. The mutation (W) at the glycosylation site destroys the EcoRI site at nucleotide positions 1032-1037. The presence of the mutation is confirmed by DNA sequencing. One plasmid DNA with the mutation is referred to as pJDB207/PH05-I-UPA-W.

In an analogous way PstI-BamHI fragments of M13mp18/UPA-P, M13mp18/UPA-LG and M13mp18/UPA-LS are used for the construction of pJDB207/PH05-I-UPA-P, pJDB207/PH05-I-UPA-LG and pJDB207/PH05-I-UPA-LS, respectively.

Example 24

Construction of plasmid pJDB207/PH05-I-UPA-LGP

To prevent proteolytic cleavage of scu-PA, the mutations of the amino acid sequence at position 135 (Lys→Gly) and at position 157 (Phe→Asp) are combined and encoded in plasmid pJDB207/PH05-I-UPA-LGP.

Plasmid pJDB207/PH05-I-UPA-LG (see Example 23) is cut with SalI and BalI. The 1.3 kb SalI-BalI fragment contains the SalI-BamHI sequence of pBR322, the PH05 promoter, the invertase signal sequence and the u-PA coding sequence up to the BalI site carrying the Gly135 mutation.

Plasmid pJDB207/PH05-I-UPA-P (see Example 23) is digested with BalI and BamHI. The 0.7 kb BalI-BamHI fragment is an internal fragment of the u-PA coding sequence carrying the Asp157 mutation.

The 1.3 kb SalI-BalI fragment, the 0.7 kb BalI-BamHI fragment and the 6.6 kb SalI-BamHI vector fragment (Example 23) are ligated. Competent cells of E. coli HB101 are transformed. Plasmid DNA of transformants is isolated and analyzed by restriction digests and DNA sequencing. A single clone with the expected nucleotide sequence coding for the mutations Gly135 and Asp157 is selected and referred to as pJDB207/PH05-I-UPA-LGP.

In an analogous way pJDB207/PH05-I-UPA-LSP is constructed using the SalI-BalI fragment of pJDB207/PH05-I-UPA-LS.

Example 25

Construction of plasmid pJDB207/PH05-I-UPA-LGPW coding for [Gly135.Asp157,Gln302]-u-PA The combination of three mutations in the u-PA amino acid sequence at positions 135, 157 and 302 results in [Gly135,Asp157,Gln302]-u-PA. This new urokinase molecule has the proteolytic cleavage sites at position 135 (Lys→Gly) and 157 (Phe→Asp) as well as the glycosylation site at position 302 (Asn→Gln) eliminated by mutation.

Plasmid pJDB207/PH05-I-UPA-LGPW codes for the urokinase mutant and is constructed in the following way:

Plasmid pJDB207/PH05-I-UPA-LGP is digested with SalI and XhoI. The 2.2 kb SalI-XhoI fragment is isolated, electroeluted from the agarose gel, purified by DE52 chromatography and precipitated in ethanol. This DNA fragment contains three MstI sites in the PH05 promoter and the u-PA sequence. 3 μg of the 2.2 kb SalI-XhoI fragment are partially digested with 3 units of MstI for 1 h at 37° C. The reaction products are separated on a preparative 0.8% agarose gel and the 1.7 kb SalI-MstI fragment is isolated and electroeluted from the gel. The DNA fragment contains the SalI-BamHI sequence of pBR322, the PH05 promoter, the invertase signal sequence and the u-PA coding sequence up to the MstI site at nucleotide position 935.

5 μg of RF-DNA of M13mp18/UPA-W (see Example 19) are digested with BamHI and MstI. After adding 2 μg of RNase (Serva) and incubating 5 min at 37° C. the 387 bp MstI-BamHI fragment is isolated on a preparative 0.8% agarose gel. The DNA fragment is electroeluted and precipitated in ethanol. The fragment contains the mutation AAT→CAA at nucleotide positions 1033-1035 (Asn302→Gln) in the urokinase B-chain.

The 1.7 kb SalI-MstI fragment, the 387 bp MstI-BamHI fragment and the 6.6 kb SalI-BamHI vector fragment (Example 23) are ligated. Competent cells of E. coli HB101 are transformed with an aliquot of the ligation mixture. Plasmid DNA of amp$^R$ transformants is isolated and analysed by HindIII and EcoRI restriction digests and by DNA sequencing. A single clone with the expected nucleotide sequence of its u-PA insert coding for the mutations Gly135, Asp157 and Gln302 is selected and referred to as pJDB207/PH05-I-UPA-LGPW.

In an analogous way pJDB207/PH05-I-UPA-LSPW is constructed using the SalI-MstI fragment of pJDB207/PH05-I-UPA-LSP.

Example 26

Transformation of S. cerevisiae strains HT246 and GRF18 and cultivation of the transformed strains Saccharomyces cerevisiae strains HT246 and GRF18 are transformed with plasmids
pJDB207/PH05-I-UPA-W
pJDB207/PH05-I-UPA-P
pJDB207/PH05-I-UPA-LG
pJDB207/PH05-I-UPA-LS
pJDB207/PH05-I-UPA-LGP
pJDB207/PH05-I-UPA-LSP
pJDB207/PH05-I-UPA-LGPW
pJDB207/PH05-I-UPA-LSPW using the transformation protocol described by Hinnen et al. [Proc. Natl. Acad. Sci. USA 75, 1929 (1978)]. Transformed yeast cells are selected on yeast minimal media plates deficient in leucine. Single transformed yeast colonies are isolated and referred to as Saccharomyces cerevisiae HT246/pJDB207/PH05-I-UPA-W
Saccharomyces cerevisiae HT246/pJDB207/PH05-I-UPA-P
Saccharomyces cerevisiae HT246/pJDB207/PH05-I-UPA-LG
Saccharomyces cerevisiae HT246/pJDB207/PH05-I-UPA-LS
Saccharomyces cerevisiae HT246/pJDB207/PH05-I-UPA-LGP
Saccharomyces cerevisiae HT246/pJDB207/PH05-I-UPA-LSP
Saccharomyces cerevisiae HT246/pJDB207/PH05-I-UPA-LGPW
Saccharomyces cerevisiae HT246/pJDB207/PH05-I-UPA-LSPW
Saccharomyces cerevisiae GRF18/pJDB207/PH05-I-UPA-W
Saccharomyces cerevisiae GRF18/pJDB207/PH05-I-UPA-P
Saccharomyces cerevisiae GRF18/pJDB207/PH05-I-UPA-LG
Saccharomyces cerevisiae GRF18/pJDB207/PH05-I-UPA-LS
Saccharomyces cerevisiae GRF18/pJDB207/PH05-I-UPA-LGP
Saccharomyces cerevisiae GRF18/pJDB207/PH05-I-UPA-LSP
Saccharomyces cerevisiae GRF18/pJDB207/PH05-I-UPA-LGPW
Saccharomyces cerevisiae GRF18/pJDB207/PH05-I-UPA-LSPW.

The strains are cultured in an analogous manner as described in Example 14. The scu-PA mutant proteins are isolated in an analogous manner as described in Examples 16 or 18.

Example 27

First pharmaceutical composition for parenteral administration

A solution for parenteral administration is prepared by dissolving 3 mg of purified scu-PA, 25 mg mannitol and 45 mg sodium chloride in 5 ml sterilized water and admixing the resulting solution with a suitable volume of 5% glucose solution. The solution is sterilized by filtration through a 0.22 μm membrane filter.

Example 28

Second pharmaceutical composition for parenteral administration (dispersion for injection)

169.3 mg soybean lecithin (soybean phosphatide NC 95, manufacturer: Nattermann, Cologne, Germany; purity 90-96%; composition of fatty acids: linoleic acid 61-71%, linolenic acid 4-7%, oleic acid 6-13%, palmitic acid 10-15%, stearic acid 1.5-3.5%) and 92.7 mg pure sodium glycocholate are dissolved in 752.5 ml of sterilized water. The solution is adjusted to pH 7.4 with 1 N NaOH. 10 mg of lyophilized scu-PA is added. The mixture is stirred until a clear solution has been obtained. The solution is sterilized by filtration through a 0.22 μm membrane filter and filled into ampoules.

Pharmaceutical compositions containing scu-PA mutants as active ingredient are prepared in an analogous manner as described in Examples 27 and 28.

Deposition of microorganisms

The following microorganism strains were deposited at the Deutsche Sammlung von Mikroorganismen (DSM),
* Grisebachstrasse 8, D-3400 Göttingen,
** Mascheroder Weg 1b, D-3300 Braunschweig (deposition dates and accession numbers given):
* *Saccharomyces cerevisiae* HT246: Apr. 15, 1987; DSM 4084;
** *Escherichia coli* HB101/pCS16: Oct. 23, 1987; DSM 4294;
** *Escherichia coli* HB101/p31R/SS-TPAΔ2: Oct. 23, 1987; DSM 4295;
** *Escherichia coli* HB101/pcUK176: Oct. 23, 1987; DSM 4290;
** *Escherichia coli* JM109/pDP38: Feb. 19, 1988; DSM 4414.

We claim:

1. A method for the production of biologically active human single chain urokinase-type plasminogen activator the *S. cerevisiae* GAPDH-promoter, a DNA segment consisting of a firs DNA sequence encoding the invertase signal sequence, upstream of and in reading frame with a second DNA sequence coding for said urokinase-type plasminogen activator, which DNA segment is under transcriptional control of said GAPDH-promoter, and a DNA sequence comprising transcription termination signals of the *S. cerevisiae* PH05 gene, and isolating said urokinase-type plasminogen activator from the cell interior.

2. A hybrid vector for use in *S. cerevisiae*, comprising an expression cassette consisting of the *S. cerevisiae* GAPDH-promoter, a DNA segment consisting of a first DNA sequence encoding the invertase signal sequence, upstream of and in reading frame with a second DNA sequence coding for human urokinase-type plasminogen activator, which DNA segment is under transcriptional control of said GAPDH-promoter, and a DNA sequence comprising transcription termination signals of the *S. cerevisiae* PH05 gene.

3. A transformed strain of *S. cerevisiae* comprising a hybrid vector according to claim 2.

4. A method according to claim 1 for the production of a plasminogen activator of the formula I

| | | | | | | | Ser | Asn | Glu | Leu | His | Gln | Val |
|---|---|---|---|---|---|---|---|---|---|---|---|---|---|
| Pro | Ser | Asn | Cys | Asp | Cys | Leu | Asn | Gly | Gly | Thr | Cys | Val | Ser | Asn |
| Lys | Tyr | Phe | Ser | Asn | Ile | His | Trp | Cys | Asn | Cys | Pro | Lys | Lys | Phe |
| Gly | Gly | Gln | His | Cys | Glu | Ile | Asp | Lys | Ser | Lys | Thr | Cys | Tyr | Glu |
| Gly | Asn | Gly | His | Phe | Tyr | Arg | Gly | Lys | Ala | Ser | Thr | Asp | Thr | Met |
| Gly | Arg | Pro | Cys | Leu | Pro | Trp | Asn | Ser | Ala | Thr | Val | Leu | Gln | Gln |
| Thr | Tyr | His | Ala | His | Arg | Ser | Asp | Ala | Leu | Gln | Leu | Gly | Leu | Gly |
| Lys | His | Asn | Tyr | Cys | Arg | Asn | Pro | Asp | Asn | Arg | Arg | Arg | Pro | Trp |
| Cys | Tyr | Val | Gln | Val | Gly | Leu | Lys | Pro | Leu | Val | Gln | Glu | Cys | Met |
| Val | His | Asp | Cys | Ala | Asp | Gly | $X_1$ | $X_2$ | Pro | Ser | Ser | Pro | Pro | Glu |
| Glu | Leu | Lys | Phe | Gln | Cys | Gly | Gln | Lys | Thr | Leu | Arg | Pro | $Y_1$ | $Y_2$ |
| $Y_3$ | Ile | Ile | Gly | Gly | Glu | Phe | Thr | Thr | Ile | Glu | Asn | Gln | Pro | Trp |
| Phe | Ala | Ala | Ile | Tyr | Arg | Arg | His | Arg | Gly | Gly | Ser | Val | Thr | Tyr |
| Val | Cys | Gly | Gly | Ser | Leu | Ile | Ser | Pro | Cys | Trp | Val | Ile | Ser | Ala |
| Thr | His | Cys | Phe | Ile | Asp | Tyr | Pro | Lys | Lys | Glu | Asp | Tyr | Ile | Val |
| Tyr | Leu | Gly | Arg | Ser | Arg | Leu | Asn | Ser | Asn | Thr | Gln | Gly | Glu | Met |
| Lys | Phe | Glu | Val | Glu | Asn | Leu | Ile | Leu | His | Lys | Asp | Tyr | Ser | Ala |
| Asp | Thr | Leu | Ala | His | His | Asn | Asp | Ile | Ala | Leu | Leu | Lys | Ile | Arg |
| Ser | Lys | Glu | Gly | Arg | Cys | Ala | Gln | Pro | Ser | Arg | Thr | Ile | Gln | Thr |
| Ile | Cys | Leu | Pro | Ser | Met | Tyr | Asn | Asp | Pro | Gln | Phe | Gly | Thr | Ser |
| Cys | Glu | Ile | Thr | Gly | Phe | Gly | Lys | Glu | $Z_1$ | Ser | $Z_2$ | Asp | Tyr | Leu |
| Tyr | Pro | Glu | Gln | Leu | Lys | Met | Thr | Val | Val | Lys | Leu | Ile | Ser | His |
| Arg | Glu | Cys | Gln | Gln | Pro | His | Tyr | Tyr | Gly | Ser | Glu | Val | Thr | Thr |
| Lys | Met | Leu | Cys | Ala | Ala | Asp | Pro | Gln | Trp | Lys | Thr | Asp | Ser | Cys |
| Gln | Gly | Asp | Ser | Gly | Gly | Pro | Leu | Val | Cys | Ser | Leu | Gln | Gly | Arg |
| Met | Thr | Leu | Thr | Gly | Ile | Val | Ser | Trp | Gly | Arg | Gly | Cys | Ala | Leu |
| Lys | Asp | Lys | Pro | Gly | Val | Tyr | Thr | Arg | Val | Ser | His | Phe | Leu | Pro |
| Trp | Ile | Arg | Ser | His | Thr | Lys | Glu | Glu | Asn | Gly | Leu | Ala | Leu | | in which $X_1$ and $X_2$ represent, $Y_1$ is Arg, $Y_2$ is Phe, $Y_3$ is Lys, $Z_1$ is Asn which is yeast-specifically glycosylated, and $Z_2$ is Thr.

* * * * *

UNITED STATES PATENT AND TRADEMARK OFFICE
CERTIFICATE OF CORRECTION

PATENT NO. : 5,175,105
DATED : December 29, 1992
INVENTOR(S) : Bernd Meyhack, et. al.

It is certified that error appears in the above-indentified patent and that said Letters Patent is hereby corrected as shown below:

Column 38, line 1, between "tor" and "the *S. cerevisiae*" please insert --, which method consists essentially of culturing under appropriate nutrient conditions a strain of *Saccharomyces cerevisiae* transformed with a hybrid vector comprising an expression cassette consisting of--.

Column 38, line 2, change "firs" to "first".

Signed and Sealed this

Twenty-sixth Day of April, 1994

Attest:

BRUCE LEHMAN

*Attesting Officer*     *Commissioner of Patents and Trademarks*